(12) United States Patent
Phillips et al.

(10) Patent No.: US 7,214,688 B2
(45) Date of Patent: May 8, 2007

(54) COMPOUNDS

(75) Inventors: Eifion Phillips, Wilmington, DE (US); Richard Schmiesing, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/325,787

(22) Filed: Jan. 5, 2006

(65) Prior Publication Data

US 2006/0128749 A1 Jun. 15, 2006

Related U.S. Application Data

(60) Division of application No. 10/123,856, filed on Apr. 15, 2002, now Pat. No. 7,001,914, which is a continuation of application No. PCT/SE01/00329, filed on Feb. 15, 2001.

(30) Foreign Application Priority Data

Feb. 18, 2000 (SE) .................... 0000540

(51) Int. Cl.
*A61K 31/46* (2006.01)
*C07D 453/02* (2006.01)

(52) U.S. Cl. .................. 514/305; 546/133; 514/305
(58) Field of Classification Search ............ 546/133; 514/305
See application file for complete search history.

(56) References Cited

U.S. PATENT DOCUMENTS

| 4,657,911 A | 4/1987 | Imbert et al. |
| 6,492,385 B2 | 12/2002 | Myers et al. |

FOREIGN PATENT DOCUMENTS

| EP | 0190920 A2 | 8/1986 |
| EP | 0327335 A1 | 8/1989 |
| EP | 0546181 A1 | 6/1993 |
| EP | 1219622 A2 | 7/2002 |
| GB | 1416872 A | 12/1975 |
| WO | WO01/36417 A1 * | 5/2001 |
| WO | WO 0192259 A1 | 12/2001 |
| WO | WO 0192260 A1 | 12/2001 |
| WO | WO 0192261 A1 | 12/2001 |
| WO | WO 0198253 A2 | 12/2001 |
| WO | WO 0215662 A2 | 2/2002 |
| WO | WO 0216355 A2 | 2/2002 |
| WO | WO 0216356 A2 | 2/2002 |
| WO | WO 0216357 A2 | 2/2002 |
| WO | WO 0216358 A2 | 2/2002 |
| WO | WO 02177358 A2 | 2/2002 |
| WO | WO 0220521 A1 | 3/2002 |
| WO | WO 0136417 A1 | 5/2002 |
| WO | WO 0244176 A1 | 6/2002 |

OTHER PUBLICATIONS

STN International, Caplus accession No. 1993:213064, document No. 118:213064, Takeda Chem Industries, Ltd: Preparation of five-membered heterocyclic amide derivatives, JP, A2; 04247081, Sep. 3, 1992.

STN International, Caplus accession No. 1996:383036, document No. 125: 167754, Brown, George R. et al: Synthesis and Activity of a Novel Series of 3-Biarylquinuclidine Squalene Synthase Inhibitors, J. Med. Chem (1996), 39(15), 2971-2979.

"Reach-Through Claims," internet article published Apr. 2, 2002, Baker Botts, LLP; http://bakerbotts.com/news/inprint/reachthroughclaims.

* cited by examiner

*Primary Examiner*—Kamal A. Saeed
*Assistant Examiner*—Janet L Coppins
(74) *Attorney, Agent, or Firm*—Kenneth F. Mitchell

(57) ABSTRACT

Compounds of formula I:

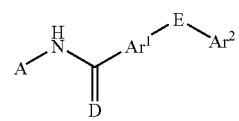

wherein A, D, $Ar^1$, E and $Ar^2$ are as defined in the specification, processes for preparing them, pharmaceutical compositions containing them and their use in therapy, especially in the treatment or prophylaxis of psychotic and intellectual impairment disorders.

21 Claims, No Drawings

COMPOUNDS

RELATED APPLICATIONS

This is an RCE of U.S. application Ser. No. 11/325,787, filed Jan. 5, 2006, allowed, which is a division of U.S. application Ser. No. 10/123,856, filed Apr. 15, 2002, now U.S. Pat. No. 7,001,914 B2, which is a continuation of International Application PCT/SE01/00329 filed Feb. 15, 2001, which designates the United States of America, which claims priority under the Paris Convention of Application No. 0000540-5 filed in Sweden on Feb. 18, 2000.

TECHNICAL FIELD

This invention relates to novel biarylcarboxamides or pharmaceutically-acceptable salts thereof, processes for preparing them, pharmaceutical compositions containing them and their use in therapy. A further object is to provide active compounds that are potent ligands for nicotinic acetylcholine receptors (nAChRs).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al. (1994) "Neuronal Nicotinic Acetylcholine Receptors," Drug News & Perspectives, vol. 7, pp. 205–223.

DISCLOSURE OF THE INVENTION

According to the invention, it has been found that compounds of formula I:

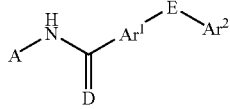

I wherein:

A represents:

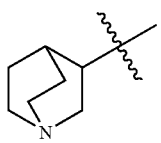

II

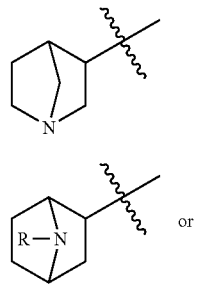

III

IV

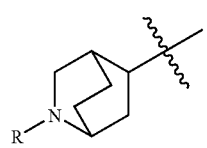

or

V

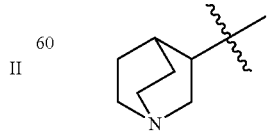

D represents oxygen or sulfur;

E represents a single bond, oxygen, sulfur, or $NR^{10}$;

R represents hydrogen or methyl;

$Ar^1$ represents a 5- or 6-membered aromatic or heteroaromatic ring containing zero to three nitrogen atoms, zero or one oxygen atom, and zero or one sulfur atom;

$Ar^2$ represents a 5- or 6-membered aromatic or heteroaromatic ring containing zero to three nitrogen atoms, zero or one oxygen atom, and zero or one sulfur atom, or; an 8-, 9- or 10-membered fused aromatic or heteroaromatic ring system containing zero to three nitrogen atoms, zero to one oxygen atom, and zero to one sulfur atom;

wherein when $Ar^2$ is unsubstituted phenyl, $Ar^1$ is not pyrazolyl; the aromatic rings $Ar^1$ and $Ar^2$ optionally substituted with one to three substituents selected from: halogen, $C_{1-4}$alkyl, $C_{2-4}$alkenyl, $C_{2-4}$alkynyl, CN, $NO_2$, $NR^1R^2$, $CH_2NR^1R^2$, $OR^3CH_2OR^3$, $CO_2R^4$, and $CF_3$; but if $Ar^1$ is phenyl and $Ar^2$ is quinolynyl, then $Ar^2$ is substituted with 0, 1, 2 or 3 substituents selected from $C_{1-4}$alkyl, $C_{2-4}$alkenyl, $C_{2-4}$alkynyl, CN, $NO_2$, $NR^1R^2$, $CH_2NR^1R^2$, $OR^3$, $CH_2OR^3$ and $CO_2R^4$;

$R^1$, $R^2$, and $R^3$ are independently $C_{1-4}$alkyl, aryl, heteroaryl, $C(O)R^5$, $C(O)NHR^6$, $C(O)R^7$, $SO_2R^8$ or $R^1$ and $R^2$ may together be $(CH_2)_jG(CH_2)_k$ where G is oxygen, sulfur, $NR^9$, or a bond;

j is 2, 3 or 4;

k is 0, 1 or 2;

$R^4$, $R^5$, $R^6$, $R^7$, $R^8$, $R^9$, and $R^{10}$, are independently $C_{1-4}$alkyl, aryl, or heteroaryl;

or an enantiomer thereof, or pharmaceutically-acceptable salts thereof, with the provisos that:

if D represents oxygen, E represents a single bond, and A represents:

II and either $Ar^1$ or $Ar^2$ represents a pyrazole ring, then all optional substituents on the pyrazole ring are hydrogen; and if Ar¹ represents a pyridine ring, Ar² represents an aryl ring, and A represents:

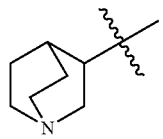

then all optional substituents on the pyridine ring shall be hydrogen; and formula I does not represent:

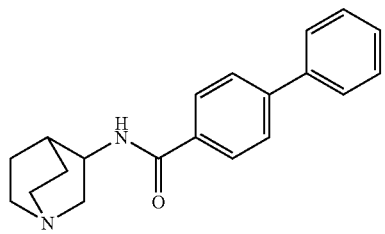

are potent ligands for nicotinic acetylcholine receptors.

Unless otherwise indicated, the $C_{1-4}$alkyl groups referred to herein, e.g., methyl, ethyl, n-propyl, n-butyl, i-propyl, i-butyl, t-butyl, s-butyl, whether alone or part of another group, may be straight-chained or branched, and the $C_{3-4}$ alkyl groups may also be cyclic, e.g., cyclopropyl, cyclobutyl. Alkyl groups referred to herein may optionally be substituted with one to three halogen atoms.

Unless otherwise indicated, aryl refers to a phenyl ring which may optionally be substituted with one to three of the following substituents selected from: halogen, $C_{1-4}$alkyl, $C_{2-4}$alkenyl, $C_{2-4}$alkynyl, $NR^1R^2$, $CH_2NR^1R^2$, $OR^3$, $CH_2OR^3$, $CO_2R^4$CN, $NO_2$, and $CF_3$.

Unless otherwise indicated, heteroaryl refers to a 5- or 6-membered aromatic or heteroaromatic ring containing zero to three nitrogen atoms, zero or one oxygen atom, and zero or one sulfur atom, provided that the ring contains at least one nitrogen, oxygen, or sulfur atom, which may optionally be substituted with one or more substituents selected from: halogen, $C_{1-4}$alkyl, $C_{2-4}$alkenyl, $C_{2-4}$alkynyl, $NR^1R^2$, $CH_2NR^1R^2$, $OR^3$, $CH_2OR^3$, $CO_2R^4$, CN, $NO_2$, and $CF_3$.

Unless otherwise indicated, halogen refers to fluorine, chlorine, bromine, or iodine.

Pharmaceutically-acceptable derivatives include solvates and salts. For example, the compounds of formula I can form acid addition salts with acids, such as the conventional pharmaceutically-acceptable acids, for example, maleic, hydrochloric, hydrobromic, phosphoric, acetic, fumaric, salicylic, citric, lactic, mandelic, tartaric and methanesulfonic acids.

Preferred compounds of the invention are compounds according to formula I wherein A represents:

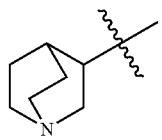

or an enantiomer thereof, and pharmaceutically-acceptable salts thereof.

Preferred embodiments of the invention include compounds of formula I wherein D represents oxygen; or an enantiomer thereof, and pharmaceutically-acceptable salts thereof.

Preferred embodiments of the invention include compounds of formula I wherein E represents a single bond; or an enantiomer thereof, and pharmaceutically-acceptable salts thereof. Preferred embodiments of the invention include compounds of formula I wherein E represents oxygen or $NR^{10}$; or an enantiomer thereof, and pharmaceutically-acceptable salts thereof.

Preferred embodiments of the invention include compounds of formula I wherein Ar¹ represents a 5- or 6-membered aromatic or heteroaromatic ring containing zero or one nitrogen atom, zero or one oxygen atom, and zero or one sulfur atom; or an enantiomer thereof, and pharmaceutically-acceptable salts thereof. Among these, compounds in which Ar¹ represents a benzene ring, furan ring or thiophene ring, are particularly preferred.

Preferred embodiments of the invention include compounds of formula I wherein Ar² represents a 5- or 6-membered aromatic or heteroaromatic ring containing zero to three nitrogen atoms, zero or one oxygen atom, and zero or one sulfur atom; or an enantiomer thereof, and pharmaceutically-acceptable salts thereof. Among these, compounds in which Ar² represents a benzene ring, furan ring, thiophene ring, or pyridine ring are particularly preferred.

Preferred embodiments of the invention include compounds of formula I, wherein the aromatic ring Ar¹ is substituted with -EAr² and the carboxamide, or thiocarboxamide group, C(=D)NHA, but no further substituents; or an enantiomer thereof, and pharmaceutically-acceptable salts thereof.

Preferred embodiments of the invention include compounds in which the -EAr² and the carboxamide or thiocarboxamide group, C(=D)NHA, substituents on Ar¹ are positioned in a 1,3-relationship relative to each other; or an enantiomer thereof, and pharmaceutically-acceptable salts thereof.

Preferred embodiments of the invention include compounds of formula I wherein Ar¹ or Ar² is substituted with zero or one substituents selected from: halogen, $C_{1-4}$alkyl, $C_{2-4}$alkenyl, $C_{2-4}$alkynyl, CN, $NO_2$, $NR^1R^2$, $CH_2NR^1R^2$, $OR^3$, $CH_2OR^3$, $CO_2R^4$, and $CF_3$; or an enantiomer thereof, and pharmaceutically-acceptable salts thereof.

Particularly preferred embodiments of the invention also include compounds of formula I wherein A represents:

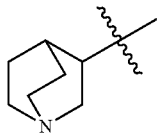

II

D represents oxygen;

E represents a single bond;

Ar¹ represents a 5- or 6-membered aromatic or heteroaromatic ring containing zero or one nitrogen atom, zero or one oxygen atom, and zero or one sulfur atom, and most preferably represents a benzene ring, furan ring or thiophene ring;

Ar² represents a 5- or 6-membered aromatic or heteroaromatic ring containing zero to three nitrogen atoms, zero or one oxygen atom, and zero or one sulfur atom;

The aromatic ring Ar¹ is substituted with -EAr² and the carboxamide group, C(=O)NHA, but no further substituents, and these substituents on Ar¹ are most preferably positioned in a 1,3-relationship relative to each other;

Ar² is substituted with zero or one substituents selected from: halogen, $C_{1-4}$alkyl, $C_{2-4}$alkenyl, $C_{2-4}$alkynyl, CN, $NO_2$, $NR^1R^2$, $CH_2NR^1R^2$, $OR^3$, $CH_2OR^3$, $CO_2R^4$, and $CR_3$; and $CF_3$; or an enantiomer thereof, and pharmaceutically-acceptable salts thereof.

Particularly preferred embodiments of the invention include compounds of formula I wherein A represents:

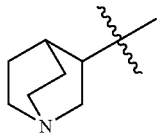

II

D represents oxygen;

E represents oxygen, or NH;

Ar¹ represents a 5- or 6-membered aromatic or heteroaromatic ring containing zero or one nitrogen atom, zero or one oxygen atom, and zero or one sulfur atom, and more preferably represents a benzene ring, furan ring or thiophene ring;

Ar² represents a 5- or 6-membered aromatic or heteroaromatic ring containing zero to three nitrogen atoms, zero or one oxygen atom, and zero or one sulfur atom;

The aromatic ring Ar¹ is substituted with -EAr² and the carboxamide group, C(=O)NHA, but no further substituents, and these substituents on Ar¹ are more preferably positioned in a 1,3-relationship relative to each other;

Ar² is substituted with zero or one substituents selected from: halogen, $C_{1-4}$alkyl, $C_{2-4}$alkenyl, $C_{2-4}$alkynyl, CN, $NO_2$, $NR^1R^2$, $CH_2NR^1R^2$, $OR^3$, $CH_2OR^3$, $CO_2R^4$, and $CF_3$; or an enantiomer thereof, and pharmaceutically-acceptable salts thereof.

Preferred embodiments of the invention include compounds according to formula I wherein A represents:

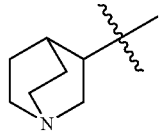

II and the configuration of the carbon atom in the quinuclidine to which the amide nitrogen is attached is (R), and pharmaceutically-acceptable salts thereof.

Preferred compounds of the invention include the following:

N-(1-Azabicyclo[2.2.2]oct-3-yl)(5-phenylfuran-2-carboxamide);

N-(1-Azabicyclo[2.2.2]oct-3-yl)(5-(3-fluorophenyl)furan-2-carboxamide);

N-(1-Azabicyclo[2.2.2]oct-3-yl)(3-(3-thienyl)benzamide);

N-(1-Azabicyclo[2.2.2]oct-3-yl)(3-phenylbenzamide);

N-(1-Azabicyclo[2.2.2]oct-3-yl)(3-(3-pyridyl)benzamide);

N-(1-Azabicyclo[2.2.2]oct-3-yl)(5-phenylthiophene-2-carboxamide);

N-(1-Azabicyclo[2.2.2]oct-3-yl)(3-(3-methoxyphenyl)benzamide);

N-(1-Azabicyclo[2.2.2]oct-3-yl)(3-(2-methoxyphenyl)benzamide);

N-(1-Azabicyclo[2.2.2]oct-3-yl)(3-(3-(N-acetylamino)phenyl)benzamide);

N-(1-Azabicyclo[2.2.2]oct-3-yl)(3-(3-fluorophenyl)benzamide);

N-(1-Azabicyclo[2.2.2]oct-3-yl)(3-(3-methylphenyl)benzamide);

N-(1-Azabicyclo[2.2.2]oct-3-yl)(3-(2-thienyl)benzamide);

N-(1-Azabicyclo[2.2.2]oct-3-yl)(3-(3,5-dichlorophenyl)benzamide);

N-(1-Azabicyclo[2.2.2]oct-3-yl)(3-(2-naphthyl)benzamide);

N-(1-Azabicyclo[2.2.2]oct-3-yl)(3-(4-fluorophenyl)benzamide);

N-(1-Azabicyclo[2.2.2]oct-3-yl)(5-(3-pyridyl)furan-2-carboxamide);

N-(1-Azabicyclo[2.2.2]oct-3-yl)(5-(3-thienyl)furan-2-carboxamide);

N-(1-Azabicyclo[2.2.2]oct-3-yl)(5-(2-benzo[b]furanyl)furan-2-carboxamide);

N-(1-Azabicyclo[2.2.2]oct-3-yl)(5-(4-pyridyl)furan-2-carboxamide);

N-(1-Azabicyclo[2.2.2]oct-3-yl)(5-(2-thienyl)furan-2-carboxamide);

N-(1-Azabicyclo[2.2.2]oct-3-yl)(5-(3-methoxyphenyl)furan-2-carboxamide);

N-(1-Azabicyclo[2.2.2]oct-3-yl)(5-(2-methoxyphenyl)furan-2-carboxamide);

N-(1-Azabicyclo[2.2.2]oct-3-yl)(5-(4-fluorophenyl)furan-2-carboxamide);

N-(1-Azabicyclo[2.2.2]oct-3-yl)(5-(2-naphthyl)furan-2-carboxamide);

N-(1-Azabicyclo[2.2.2]oct-3-yl)(5-(3-methylphenyl)furan-2-carboxamide);

N-(1-Azabicyclo[2.2.2]oct-3-yl)(5-(3-furyl)furan-2-carboxamide);

N-(1-Azabicyclo[2.2.2]oct-3-yl)(5-(2-furyl)furan-2-carboxamide);

N-(1-Azabicyclo[2.2.2]oct-3-yl)(5-(2-pyridyl)furan-2-carboxamide);

N-(1-Azabicyclo[2.2.2]oct-3-yl)(5-(4-pyridyl)thiophene-2-carboxamide);

N-(1-Azabicyclo[2.2.2]oct-3-yl)(5-(3-pyridyl)thiophene-2-carboxamide);

N-(1-Azabicyclo[2.2.2]oct-3-yl)(5-(2-pyridyl)thiophene-2-carboxamide);

N-(1-Azabicyclo[2.2.2]oct-3-yl)(4-(2-pyridyl)thiophene-2-carboxamide);

N-(1-Azabicyclo[2.2.2]oct-3-yl)(4-(4-pyridyl)thiophene-2-carboxamide);

N-(1-Azabicyclo[2.2.2]oct-3-yl)(4-(3-pyridyl)thiophene-2-carboxamide);

N-(1-Azabicyclo[2.2.2]oct-3-yl)(5-(3-(N-acetylamino)phenyl)furan-2-carboxamide);

N-(1-Azabicyclo[2.2.2]oct-3-yl)(5-(3-nitrophenyl)furan-2-carboxamide);

N-(1-Azabicyclo[2.2.2]oct-3-yl)(5-(3-trifluoromethylphenyl)furan-2-carboxamide);

N-(1-Azabicyclo[2.2.2]oct-3-yl)(5-(3-chlorophenyl)furan-2-carboxamide);

N-(1-Azabicyclo[2.2.2]oct-3-yl)(5-(3-(N-acetylamino)phenyl)thiophene-2-carboxamide);

N-(1-Azabicyclo[2.2.2]oct-3-yl)(5-(3-fluorophenyl)thiophene-2-carboxamide);

N-(1-Azabicyclo[2.2.2]oct-3-yl)(5-(3-methoxyphenyl)thiophene-2-carboxamide);

N-(1-Azabicyclo[2.2.2]oct-3-yl)(5-(3-ethoxyphenyl)thiophene-2-carboxamide);

N-(1-Azabicyclo[2.2.2]oct-3-yl)(5-(3,5-dimethylisoxazol-4-yl)furan-2-carboxamide);

N-(1-Azabicyclo[2.2.2]oct-3-yl)(5-(3,5-dimethylisoxazol-4-yl)thiophene-2-carboxamide);

N-(1-Azabicyclo[2.2.2]oct-3-yl)(5-(3-aminophenyl)thiophene-2-carboxamide);

N-(1-Azabicyclo[2.2.2]oct-3-yl)(5-(3-pyridyl)thiophene-3-carboxamide);

N-(1-Azabicyclo[2.2.2]oct-3-yl)(5-(4-chlorophenyl)furan-2-carboxamide);

N-(1-Azabicyclo[2.2.2]oct-3-yl)(5-(3-pyridyl)thiazole-3-carboxamide);

N-(1-Azabicyclo[2.2.2]oct-3-yl)(5-(4-pyridyl)thiazole-3-carboxamide);

N-(1-Azabicyclo[2.2.2]oct-3-yl)(5-(3-(N,N-dimethylamino)phenyl)thiophene-2-carboxamide);

N-(1-Azabicyclo[2.2.2]oct-3-yl)(5-(8-quinolinyl)thiophene-2-carboxamide);

N-(1-Azabicyclo[2.2.2]oct-3-yl)(5-phenylthiophene-3-carboxamide);

N-(1-Azabicyclo[2.2.2]oct-3-yl)(4-phenylthiophene-2-carboxamide);

N-(1-Azabicyclo[2.2.2]oct-3-yl)(5-(3-cyanophenyl)thiophene-2-carboxamide);

N-(1-Azabicyclo[2.2.2]oct-3-yl)(5-(3-(N-methylamino)phenyl)thiophene-2-carboxamide);

N-(1-Azabicyclo[2.2.2]oct-3-yl)(5-(3-hydroxyphenyl)thiophene-2-carboxamide);

N-(1-Azabicyclo[2.2.2]oct-3-yl)(5-(3-pyridylamino)thiophene-2-carboxamide);

N-(1-Azabicyclo[2.2.2]oct-3-yl)(5-(3-chlorophenyl)thiophene-2-carboxamide);

N-(1-Azabicyclo[2.2.2]oct-3-yl)(5-(3-(4-morpholinyl)phenyl)thiophene-2-carboxamide);

N-(1-Azabicyclo[2.2.2]oct-3-yl)(5-(3-(aminomethyl)phenyl)thiophene-2-carboxamide);

N-(1-Azabicyclo[2.2.2]oct-3-yl)(5-phenoxythiophene-2-carboxamide);

N-(1-Azabicyclo[2.2.2]oct-3-yl)(5-(3-aminophenyl)furan-2-carboxamide);

N-(1-Azabicyclo[2.2.2]oct-3-yl)(5-(3-(N,N-dimethylamino)phenyl)furan-2-carboxamide);

N-(1-Azabicyclo[2.2.2]oct-3-yl)(5-(3-formylphenyl)thiophene-2-carboxamide); and

N-(1-Azabicyclo[2.2.2]oct-3-yl)(5-(3-(hydroxymethyl)phenyl)thiophene-2-carboxamide).

Particularly preferred compounds of the invention include the following:

(R)-N-(1-Azabicyclo[2.2.2]oct-3-yl)(5-phenylfuran-2-carboxamide);

(R)-N-(1-Azabicyclo[2.2.2]oct-3-yl)(5-(3-fluorophenyl)furan-2-carboxamide);

(R)-N-(1-Azabicyclo[2.2.2]oct-3-yl)(3-(3-thienyl)benzamide);

(R)-N-(1-Azabicyclo[2.2.2]oct-3-yl)(3-phenylbenzamide);

(R)-N-(1-Azabicyclo[2.2.2]oct-3-yl)(3-(3-pyridyl)benzamide);

(R)-N-(1-Azabicyclo[2.2.2]oct-3-yl)(5-phenylthiophene-2-carboxamide);

(R)-N-(1-Azabicyclo[2.2.2]oct-3-yl)(3-(3-methoxyphenyl)benzamide);

(R)-N-(1-Azabicyclo[2.2.2]oct-3-yl)(3-(2-methoxyphenyl)benzamide);

(R)-N-(1-Azabicyclo[2.2.2]oct-3-yl)(3-(3-(N-acetylamino)phenyl)benzamide);

(R)-N-(1-Azabicyclo[2.2.2]oct-3-yl)(3-(3-fluorophenyl)benzamide);

(R)-N-(1-Azabicyclo[2.2.2]oct-3-yl)(3-(3-methylphenyl)benzamide);

(R)-N-(1-Azabicyclo[2.2.2]oct-3-yl)(3-(2-thienyl)benzamide);

(R)-N-(1-Azabicyclo[2.2.2]oct-3-yl)(3-(3,5-dichlorophenyl)benzamide);

(R)-N-(1-Azabicyclo[2.2.2]oct-3-yl)(3-(2-naphthyl)benzamide);

(R)-N-(1-Azabicyclo[2.2.2]oct-3-yl)(3-(4-fluorophenyl)benzamide);

(R)-N-(1-Azabicyclo[2.2.2]oct-3-yl)(5-(3-pyridyl)furan-2-carboxamide);

(R)-N-(1-Azabicyclo[2.2.2]oct-3-yl)(5-(3-thienyl)furan-2-carboxamide);

(R)-N-(1-Azabicyclo[2.2.2]oct-3-yl)(5-(2-benzo[b]furanyl)furan-2-carboxamide);

(R)-N-(1-Azabicyclo[2.2.2]oct-3-yl)(5-(4-pyridyl)furan-2-carboxamide);

(R)-N-(1-Azabicyclo[2.2.2]oct-3-yl)(5-(2-thienyl)furan-2-carboxamide);

(R)-N-(1-Azabicyclo[2.2.2]oct-3-yl)(5-(3-methoxyphenyl)furan-2-carboxamide);

(R)-N-(1-Azabicyclo[2.2.2]oct-3-yl)(5-(2-methoxyphenyl)furan-2-carboxamide);

(R)-N-(1-Azabicyclo[2.2.2]oct-3-yl)(5-(4-fluorophenyl)furan-2-carboxamide);

(R)-N-(1-Azabicyclo[2.2.2]oct-3-yl)(5-(2-naphthyl)furan-2-carboxamide);

(R)-N-(1-Azabicyclo[2.2.2]oct-3-yl)(5-(3-methylphenyl)furan-2-carboxamide);

(R)-N-(1-Azabicyclo[2.2.2]oct-3-yl)(5-(3-furyl)furan-2-carboxamide);

(R)-N-(1-Azabicyclo[2.2.2]oct-3-yl)(5-(2-furyl)furan-2-carboxamide);
(R)-N-(1-Azabicyclo[2.2.2]oct-3-yl)(5-(2-pyridyl)furan-2-carboxamide);
(R)-N-(1-Azabicyclo[2.2.2]oct-3-yl)(5-(4-pyridyl)thiophene-2-carboxamide);
(R)-N-(1-Azabicyclo[2.2.2]oct-3-yl)(5-(3-pyridyl)thiophene-2-carboxamide);
(R)-N-(1-Azabicyclo[2.2.2]oct-3-yl)(5-(2-pyridyl)thiophene-2-carboxamide);
(R)-N-(1-Azabicyclo[2.2.2]oct-3-yl)(4-(2-pyridyl)thiophene-2-carboxamide);
(R)-N-(1-Azabicyclo[2.2.2]oct-3-yl)(4-(4-pyridyl)thiophene-2-carboxamide);
(R)-N-(1-Azabicyclo[2.2.2]oct-3-yl)(4-(3-pyridyl)thiophene-2-carboxamide);
(R)-N-(1-Azabicyclo[2.2.2]oct-3-yl)(5-(3-(N-acetylamino)phenyl)furan-2-carboxamide);
(R)-N-(1-Azabicyclo[2.2.2]oct-3-yl)(5-(3-nitrophenyl)furan-2-carboxamide);
(R)-N-(1-Azabicyclo[2.2.2]oct-3-yl)(5-(3-trifluoromethylphenyl)furan-2-carboxamide);
(R)-N-(1-Azabicyclo[2.2.2]oct-3-yl)(5-(3-chlorophenyl)furan-2-carboxamide);
(R)-N-(1-Azabicyclo[2.2.2]oct-3-yl)(5-(3-(N-acetylamino)phenyl)thiophene-2-carboxamide);
(R)-N-(1-Azabicyclo[2.2.2]oct-3-yl)(5-(3-fluorophenyl)thiophene-2-carboxamide);
(R)-N-(1-Azabicyclo[2.2.2]oct-3-yl)(5-(3-methoxyphenyl)thiophene-2-carboxamide);
(R)-N-(1-Azabicyclo[2.2.2]oct-3-yl)(5-(3-ethoxyphenyl)thiophene-2-carboxamide);
(R)-N-(1-Azabicyclo[2.2.2]oct-3-yl)(5-(3,5-dimethyl-isoxazol-4-yl)furan-2-carboxamide);
(R)-N-(1-Azabicyclo[2.2.2]oct-3-yl)(5-(3,5-dimethyl-isoxazol-4-yl)thiophene-2-carboxamide);
(R)-N-(1-Azabicyclo[2.2.2]oct-3-yl)(5-(3-aminophenyl)thiophene-2-carboxamide);
(R)-N-(1-Azabicyclo[2.2.2]oct-3-yl)(5-(3-pyridyl)thiophene-3-carboxamide);
(R)-N-(1-Azabicyclo[2.2.2]oct-3-yl)(5-(4-chlorophenyl)furan-2-carboxamide);
(R)-N-(1-Azabicyclo[2.2.2]oct-3-yl)(5-(3-pyridyl)thiazole-3-carboxamide);
(R)-N-(1-Azabicyclo[2.2.2]oct-3-yl)(5-(4-pyridyl)thiazole-3-carboxamide);
(R)-N-(1-Azabicyclo[2.2.2]oct-3-yl)(5-(3-(N,N-dimethylamino)phenyl)thiophene-2-carboxamide);
(R)-N-(1-Azabicyclo[2.2.2]oct-3-yl)(5-(8-quinolinyl)thiophene-2-carboxamide);
(S)-N-(1-Azabicyclo[2.2.2]oct-3-yl)(5-(3-pyridyl)thiophene-2-carboxamide);
(S)-N-(1-Azabicyclo[2.2.2]oct-3-yl)(5-(4-pyridyl)thiophene-2-carboxamide);
(S)-N-(1-Azabicyclo[2.2.2]oct-3-yl)(5-(2-pyridyl)thiophene-2-carboxamide);
(S)-N-(1-Azabicyclo[2.2.2]oct-3-yl)(5-phenylthiophene-2-carboxamide);
(R)-N-(1-Azabicyclo[2.2.2]oct-3-yl)(5-phenylthiophene-3-carboxamide);
(R)-N-(1-Azabicyclo[2.2.2]oct-3-yl)(4-phenylthiophene-2-carboxamide);
(R)-N-(1-Azabicyclo[2.2.2]oct-3-yl)(5-(3-cyanophenyl)thiophene-2-carboxamide);
(R)-N-(1-Azabicyclo[2.2.2]oct-3-yl)(5-(3-(N-methylamino)phenyl)thiophene-2-carboxamide);
(R)-N-(1-Aza-bicyclo[2.2.2]oct-3-yl)(5-(3-hydroxyphenyl)thiophene-2-carboxamide);
(R)-N-(1-Azabicyclo[2.2.2]oct-3-yl)(5-(3-pyridylamino)thiophene-2-carboxamide);
(R)-N-(1-Azabicyclo[2.2.2]oct-3-yl)(5-(3-chlorophenyl)thiophene-2-carboxamide);
(R)-N-(1-Aza-bicyclo[2.2.2]oct-3-yl)(5-(3-(4-morpholinyl)phenyl)thiophene-2-carboxamide);
(R)-N-(1-Azabicyclo[2.2.2]oct-3-yl)(5-(3-(aminomethyl)phenyl)thiophene-2-carboxamide);
(R)-N-(1-Azabicyclo[2.2.2]oct-3-yl)(5-phenoxythiophene-2-carboxamide);
(R)-N-(1-Azabicyclo[2.2.2]oct-3-yl)(5-(3-aminophenyl)furan-2-carboxamide)
(R)-N-(1-Azabicyclo[2.2.2]oct-3-yl)(5-(3-(N,N-dimethylamino)phenyl)furan-2-carboxamide);
(R)-N-(1-azabicyclo[2.2.2]oct-3-yl)(5-(3-formylphenyl)thiophene-2-carboxamide);
(R)-N-(1-Azabicyclo[2.2.2]oct-3-yl)(5-(3-(hydroxymethyl)phenyl)thiophene-2-carboxamide);

and pharmaceutically-acceptable salts thereof.

Among these compounds, the following compounds of the invention are more particularly preferred:
(R)-N-(1-Azabicyclo[2.2.2]oct-3-yl)(5-phenylfuran-2-carboxamide);
(R)-N-(1-Azabicyclo[2.2.2]oct-3-yl)(5-(3-fluorophenyl)furan-2-carboxamide);
(R)-N-(1-Azabicyclo[2.2.2]oct-3-yl)(3-(3-thienyl)benzamide);
(R)-N-(1-Azabicyclo[2.2.2]oct-3-yl)(3-phenylbenzamide);
(R)-N-(1-Azabicyclo[2.2.2]oct-3-yl)(5-phenylthiophene-2-carboxamide);
(R)-N-(1-Azabicyclo[2.2.2]oct-3-yl)(3-(3-(N-acetylamino)phenyl)benzamide);
(R)-N-(1-Azabicyclo[2.2.2]oct-3-yl)(3-(2-thienyl)benzamide);
(R)-N-(1-Azabicyclo[2.2.2]oct-3-yl)(5-(3-pyridyl)furan-2-carboxamide);
(R)-N-(1-Azabicyclo[2.2.2]oct-3-yl)(5-(3-thienyl)furan-2-carboxamide);
(R)-N-(1-Azabicyclo[2.2.2]oct-3-yl)(5-(2-benzo[b]furanyl)furan-2-carboxamide);
(R)-N-(1-Azabicyclo[2.2.2]oct-3-yl)(5-(4-pyridyl)furan-2-carboxamide);
(R)-N-(1-Azabicyclo[2.2.2]oct-3-yl)(5-(2-thienyl)furan-2-carboxamide);
(R)-N-(1-Azabicyclo[2.2.2]oct-3-yl)(5-(3-methoxyphenyl)furan-2-carboxamide);
(R)-N-(1-Azabicyclo[2.2.2]oct-3-yl)(5-(4-fluorophenyl)furan-2-carboxamide);
(R)-N-(1-Azabicyclo[2.2.2]oct-3-yl)(5-(2-naphthyl)furan-2-carboxamide);
(R)-N-(1-Azabicyclo[2.2.2]oct-3-yl)(5-(3-methylphenyl)furan-2-carboxamide);
(R)-N-(1-Azabicyclo[2.2.2]oct-3-yl)(5-(3-furyl)furan-2-carboxamide);
(R)-N-(1-Azabicyclo[2.2.2]oct-3-yl)(5-(2-pyridyl)furan-2-carboxamide);
(R)-N-(1-Azabicyclo[2.2.2]oct-3-yl)(5-(4-pyridyl)thiophene-2-carboxamide);
(R)-N-(1-Azabicyclo[2.2.2]oct-3-yl)(5-(3-pyridyl)thiophene-2-carboxamide);
(R)-N-(1-Azabicyclo[2.2.2]oct-3-yl)(5-(2-pyridyl)thiophene-2-carboxamide);

(R)-N-(1-Azabicyclo[2.2.2]oct-3-yl)(4-(2-pyridyl)thiophene-2-carboxamide);
(R)-N-(1-Azabicyclo[2.2.2]oct-3-yl)(5-(3-(N-acetylamino)phenyl)furan-2-carboxamide);
(R)-N-(1-Azabicyclo[2.2.2]oct-3-yl)(5-(3-nitrophenyl)furan-2-carboxamide);
(R)-N-(1-Azabicyclo[2.2.2]oct-3-yl)(5-(3-trifluoromethylphenyl)furan-2-carboxamide);
(R)-N-(1-Azabicyclo[2.2.2]oct-3-yl)(5-(3-chlorophenyl)furan-2-carboxamide);
(R)-N-(1-Azabicyclo[2.2.2]oct-3-yl)(5-(3-(N-acetylamino)phenyl)thiophene-2-carboxamide);
(R)-N-(1-Azabicyclo[2.2.2]oct-3-yl)(5-(3-fluorophenyl)thiophene-2-carboxamide);
(R)-N-(1-Azabicyclo[2.2.2]oct-3-yl)(5-(3-methoxyphenyl)thiophene-2-carboxamide);
(R)-N-(1-Azabicyclo[2.2.2]oct-3-yl)(5-(3-ethoxyphenyl)thiophene-2-carboxamide);
(R)-N-(1-Azabicyclo[2.2.2]oct-3-yl)(5-(3,5-dimethylisoxazol-4-yl)thiophene-2-carboxamide);
(R)-N-(1-Azabicyclo[2.2.2]oct-3-yl)(5-(3-aminophenyl)thiophene-2-carboxamide);
(R)-N-(1-Azabicyclo[2.2.2]oct-3-yl)(5-(3-pyridyl)thiophene-3-carboxamide);
(R)-N-(1-Azabicyclo[2.2.2]oct-3-yl)[5-(4-chlorophenyl)furan-2-carboxamide);
(R)-N-(1-Azabicyclo[2.2.2]oct-3-yl)(5-(3-(N,N-dimethylamino)phenyl)thiophene-2-carboxamide);
(R)-N-(1-Azabicyclo[2.2.2]oct-3-yl)(5-(8-quinolinyl)thiophene-2-carboxamide);
(S)-N-(1-Azabicyclo[2.2.2]oct-3-yl)(5-(3-pyridyl)thiophene-2-carboxamide);
(S)-N-(1-Azabicyclo[2.2.2]oct-3-yl)(5-(4-pyridyl)thiophene-2-carboxamide);
(S)-N-(1-Azabicyclo[2.2.2]oct-3-yl)(5-(2-pyridyl)thiophene-2-carboxamide);
(S)-N-(1-Azabicyclo[2.2.2]oct-3-yl)(5-phenylthiophene-2-carboxamide);
(R)-N-(1-Azabicyclo[2.2.2]oct-3-yl)(5-phenylthiophene-3-carboxamide);
(R)-N-(1-Azabicyclo[2.2.2]oct-3-yl)(4-phenylthiophene-2-carboxamide);
(R)-N-(1-Azabicyclo[2.2.2]oct-3-yl)(5-(3-cyanophenyl)thiophene-2-carboxamide);
(R)-N-(1-Azabicyclo[2.2.2]oct-3-yl)(5-(3-(N-methylamino)phenyl)thiophene-2-carboxamide);
(R)-N-(1-Azabicyclo[2.2.2]oct-3-yl)(5-(3-hydroxyphenyl)thiophene-2-carboxamide);
(R)-N-(1-Azabicyclo[2.2.2]oct-3-yl)(5-(3-pyridylamino)thiophene-2-carboxamide);
(R)-N-(1-Azabicyclo[2.2.2]oct-3-yl)(5-(3-(4-morpholinyl)phenyl)thiophene-2-carboxamide);
(R)-N-(1-Azabicyclo[2.2.2]oct-3-yl)(5-(3-(aminomethyl)phenyl)thiophene-2-carboxamide);
(R)-N-(1-Azabicyclo[2.2.2]oct-3-yl)(5-phenoxythiophene-2-carboxamide);
(R)-N-(1-Azabicyclo[2.2.2]oct-3-yl)(5-(3-aminophenyl)furan-2-carboxamide);
(R)-N-(1-Azabicyclo[2.2.2]oct-3-yl)(5-(3-(N,N-dimethylamino)phenyl)furan-2-carboxamide);
(R)-N-(1-Azabicyclo[2.2.2]oct-3-yl)(5-(3-(hydroxymethyl)phenyl)thiophene-2-carboxamide);
and pharmaceutically-acceptable salts thereof.

Among these compounds, the following compounds of the invention are most particularly preferred:
(R)-N-(1-Azabicyclo[2.2.2]oct-3-yl)(5-(3-fluorophenyl)furan-2-carboxamide);
(R)-N-(1-Azabicyclo[2.2.2]oct-3-yl)(5-(3-pyridyl)furan-2-carboxamide);
(R)-N-(1-Azabicyclo[2.2.2]oct-3-yl)(5-(4-pyridyl)furan-2-carboxamide);
(R)-N-(1-Azabicyclo[2.2.2]oct-3-yl)(5-(3-methoxyphenyl)furan-2-carboxamide);
(R)-N-(1-Azabicyclo[2.2.2]oct-3-yl)(5-(4-fluorophenyl)furan-2-carboxamide);
(R)-N-(1-Azabicyclo[2.2.2]oct-3-yl)(5-(4-pyridyl)thiophene-2-carboxamide);
(R)-N-(1-Azabicyclo[2.2.2]oct-3-yl)(5-(3-pyridyl)thiophene-2-carboxamide);
(R)-N-(1-Azabicyclo[2.2.2]oct-3-yl)(5-(3-(N-acetylamino)phenyl)furan-2-carboxamide);
(R)-N-(1-Azabicyclo[2.2.2]oct-3-yl)(5-(3-nitrophenyl)furan-2-carboxamide);
(R)-N-(1-Azabicyclo[2.2.2]oct-3-yl)(5-(3-trifluoromethylphenyl)furan-2-carboxamide);
(R)-N-(1-Azabicyclo[2.2.2]oct-3-yl)(5-(3-chlorophenyl)furan-2-carboxamide);
(R)-N-(1-Azabicyclo[2.2.2]oct-3-yl)(5-(3-(N-acetylamino)phenyl)thiophene-2-carboxamide);
(R)-N-(1-Azabicyclo[2.2.2]oct-3-yl)(5-(3-aminophenyl)thiophene-2-carboxamide);
(R)-N-(1-Azabicyclo[2.2.2]oct-3-yl)(5-(3-pyridyl)thiophene-3-carboxamide);
(S)-N-(1-Azabicyclo[2.2.2]oct-3-yl)(5-(3-pyridyl)thiophene-2-carboxamide);
(S)-N-(1-Azabicyclo[2.2.2]oct-3-yl)(5-(2-pyridyl)thiophene-2-carboxamide);
(R)-N-(1-Azabicyclo[2.2.2]oct-3-yl)(4-phenylthiophene-2-carboxamide);
(R)-N-(1-Azabicyclo[2.2.2]oct-3-yl)(5-(3-cyanophenyl)thiophene-2-carboxamide);
(R)-N-(1-Azabicyclo[2.2.2]oct-3-yl)(5-(3-hydroxyphenyl)thiophene-2-carboxamide);
(R)-N-(1-Azabicyclo[2.2.2]oct-3-yl)(5-phenoxythiophene-2-carboxamide);
(R)-N-(1-Azabicyclo[2.2.2]oct-3-yl)(5-(3-aminophenyl)furan-2-carboxamide);
(R)-N-(1-Azabicyclo[2.2.2]oct-3-yl)(5-(3-(hydroxymethyl)phenyl)thiophene-2-carboxamide); and pharmaceutically-acceptable salts thereof.

Methods of Preparation

In the reaction schemes and text that follow, A, E, $Ar^1$, and $Ar^2$ unless otherwise indicated, are as defined above for formula I.

The compounds of formula I in which E represent a single bond may be prepared according to the following methods outlined in Scheme 1.

Scheme 1

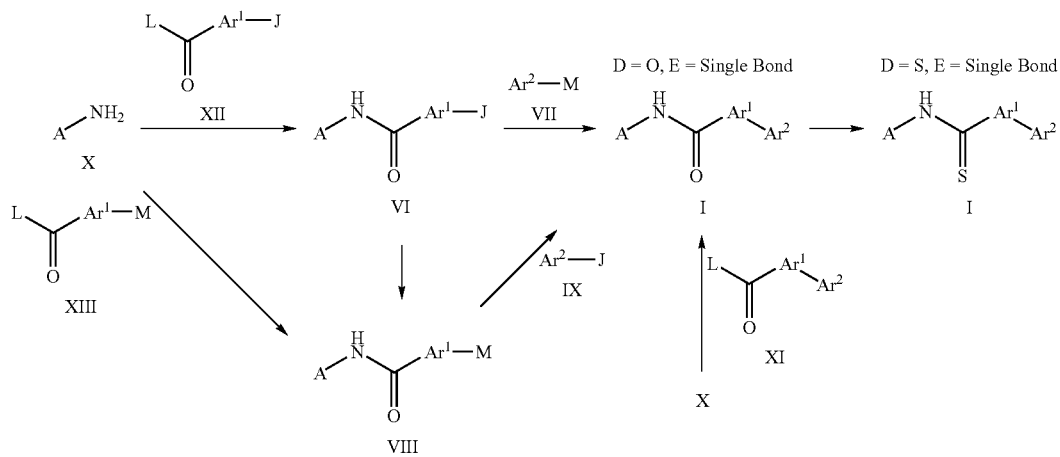

Compounds of formula I wherein D represents oxygen and E represents a single bond may be prepared from compounds of formula VI wherein J represents a halogen or $OSO_2CF_3$ substituent at the position of ring $Ar^1$ at which the bond to ring $Ar^2$ is formed, by reaction with an appropriate organometallic compound of formula VII in the presence of a suitable organometallic catalyst and solvent. Suitable compounds of formula VII include boronic acids, in which M represents $B(OH)_2$ and organotin compounds, in which M represents a suitable trialkylstannyl group, for example trimethylstannyl or tri-n-butylstannyl. Suitable organometallic catalysts include palladium (0) complexes, for example tetrakis(triphenylphosphine)palladium(0) or a combination of tris(dibenzylideneacetone)dipalladium(0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula VII is a boronic acid, the presence of a suitable base in addition to the other reagents is preferred. Suitable bases include sodium carbonate, cesium carbonate, and barium hydroxide. The reaction is carried out at a temperature of 0–120° C., and preferably at a temperature of 60–120° C.

Compounds of formula I wherein D represents oxygen and E represents a single bond may also be prepared from organometallic compounds of formula VIII by reaction with a compound of formula IX in which J represents a halogen or $OSO_2CF_3$ in the presence of a suitable organometallic catalyst and solvent. Suitable compounds of formula VIII include boronic acids, in which M represents $B(OH)_2$ and organotin compounds, in which M represents a suitable trialkylstannyl group, for example trimethylstannyl or tri-n-butylstannyl. Suitable organometallic catalysts include palladium (0) complexes, for example tetrakis(triphenylphosphine)palladium (0) or a combination of tris(dibenzylideneacetone)dipalladium (0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula VIII is a boronic acid, the presence of a suitable base in addition to the other reagents is preferred. Suitable bases include sodium carbonate, cesium carbonate, and barium hydroxide. The reaction is carried out at a temperature of 0–120° C., and preferably at a temperature of 60–120° C.

Compounds of formula I wherein D represents oxygen and E represents a single bond may also be prepared from compounds of formula X by reaction with a suitable compound of formula XI, wherein L represents a suitable leaving group, using a suitable acylation procedure. Suitable leaving groups L include: OH, halogen, OAlkyl, OAryl, OCOAlkyl, OCOAryl. A suitable acylation procedure involves treatment of a compound of formula X with a compound of formula XI at 0–120° C. in a suitable solvent. The presence of a base, or, when Y=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when L=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0–50° C., and most preferably at a temperature of 20–30° C.

Compounds of formula I in which D represents sulfur and E represents a single bond may be prepared from compounds of formula I in which D represents oxygen and E represents a single bond by reaction with a suitable sulfide in a suitable solvent. The preferred sulfides are phosphorus sulfides, in particular 4-methoxyphenylthionophosphine sulfide dimer ("Lawesson's Reagent"), and diphosphorus pentasulfide. Suitable solvents for the reaction include aryl hydrocarbon solvents, for example toluene or xylene. The reaction is performed at a temperature of 0–200° C., and preferably at a temperature of 50–180° C.

Certain compounds of formula VI wherein J represents halogen may be prepared from compounds of formula VI wherein J represents hydrogen by reaction with a suitable halogenating agent in a suitable solvent. Suitable halogenating agents include bromine. Suitable solvents include acetic acid. The reaction is preferably performed at a temperature of 0–50° C., and most preferably at a temperature of 0–25° C.

Compounds of formula VI wherein J represents $OSO_2CF_3$ may be prepared from compounds of formula VI wherein J represents OH by reaction with trifluoromethanesulfonic anhydride or other trifluoromethanesulfonylating agent in the presence of a base and a suitable solvent. Suitable bases include pyridine, and 2,6-di-t-butylpyridine. The reaction is preferably performed at a temperature of −78 to 120° C., and most preferably at a temperature of −78 to 0° C.

Compounds of formula VI wherein J represents hydrogen, halogen, OH, or $OSO_2CF_3$ may be prepared from compounds of formula X by reaction with a suitable compound of formula XII, wherein L represents a suitable leaving group and J represents hydrogen, halogen, OH, or $OSO_2CF_3$, using a suitable acylation procedure. Suitable leaving groups L include: OH, halogen, OAlkyl, OAryl, OCOAlkyl, OCOAryl. A suitable acylation procedure involves treatment of a compound of formula X with a compound of formula XII at 0–120° C. in a suitable solvent. The presence of a base, or, when L=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when Y=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0–50° C., and most preferably at a temperature of 20–30° C.

Compounds of formula VIII in which M represents $B(OH)_2$ may be prepared from compounds of formula VI in which J represents hydrogen, halogen, or $OSO_2CF_3$ by methods known to one skilled in the art. For example compounds of formula VI in which J represents hydrogen or halogen may be converted to compounds of formula VIII in which M represents $B(OH)_2$ via conversion to the corresponding aryllithium or arylmagnesium compounds followed by reaction with trimethylborate and subsequent hydrolysis of the resulting borate ester. The reaction is performed in a suitable inert solvent, for example, tetrahydrofuran. Alternatively, compounds of formula VI wherein J represents halogen or $OSO_2CF_3$ may be converted to compounds of formula VIII in which M represents $B(OH)_2$ via reaction with bis(pinacolato)diboron and an organometallic catalyst, followed by hydrolysis of the resulting borate ester. For typical procedures for effecting such conversions, see, for example, *Organic Syntheses*, 1963, Coll. Vol. 4, 68; *J. Org. Chem.* 1995, 60, 7508.

Compounds of formula VIII in which M represents a trialkylstannyl group may be prepared from compounds of formula VI in which J represents hydrogen, halogen, or $OSO_2CF_3$ by methods known to one skilled in the art. For example compounds of formula VI in which J represents hydrogen or halogen may be converted to compounds of formula VIII in which M represents a trialkylstannyl group via conversion to the corresponding aryllithium or arylmagnesium compounds followed by reaction with an appropriate trialkylstannyl halide. The reaction is performed in a suitable inert solvent, for example, tetrahydrofuran. The reaction is performed at a temperature of −78° C. to 20° C., preferably at −78° C. to 0° C. Alternatively, compounds of formula VI wherein J represents halogen or $OSO_2CF_3$ may be converted to compounds of formula VIII in which M represents a trialkylstannyl group via reaction with the appropriate bis(trialkyltin). The reaction is performed in a suitable inert solvent, for example tetrahydrofuran, in the presence of a suitable organometallic catalyst, for example tetrakis(triphenylphosphine). The reaction is performed at a temperature of 0° C. to 150° C., preferably at 20° C. to 100° C.

Compounds of formula VIII wherein M represents $B(OH)_2$ or a trialkylstannyl group may be prepared from compounds of formula X by reaction with a suitable compound of formula XIII, wherein L represents a suitable leaving group M represents $B(OH)_2$ or a trialkylstannyl group, using a suitable acylation procedure. Suitable leaving groups L include: OH, halogen, OAlkyl, OAryl, OCOAlkyl, OCOAryl. A suitable acylation procedure involves treatment of a compound of formula X with a compound of formula XIII at 0–120° C. in a suitable solvent. The presence of a base, or, when L=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when L=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0–50° C., and most preferably at a temperature of 20–30° C.

Compounds of formula XI may be prepared from compounds of formula XII wherein J represents a halogen or $OSO_2CF_3$ substituent at the position of ring $Ar^1$ at which the bond to ring $Ar^2$ is formed, by reaction with an appropriate organometallic compound of formula VII in the presence of a suitable organometallic catalyst and solvent. Suitable compounds of formula VII include boronic acids, in which M represents $B(OH)_2$ and organotin compounds, in which M represents a suitable trialkylstannyl group, for example trimethylstannyl or tri-n-butylstannyl. Suitable organometallic catalysts include palladium (0) complexes, for example tetrakis(triphenylphosphine)palladium (0) or a combination of tris(dibenzylideneacetone)dipalladium (0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula VII is a boronic acid, the presence of a suitable base in addition to the other reagents is preferred. Suitable bases include sodium carbonate, cesium carbonate, and barium hydroxide. The reaction is carried out at a temperature of 0–120° C., and preferably at a temperature of 60–120° C.

Compounds of formula XI may also be prepared from organometallic compounds of formula XIII by reaction with a compound of formula IX in which J represents a halogen or $OSO_2CF_3$ in the presence of a suitable organometallic compounds followed by reaction with trimethylborate, or via reaction with bis(pinacolato)diboron and an organometallic catalyst, followed by hydrolysis of the resulting borate ester (see, for example, *Organic Syntheses,* 1963, *Coll. Vol.* 4, 68; *J. Org. Chem.* 1995, 60, 7508). Trialkylstannanes may be synthesised from aryl or heteroaryl halides via conversion to the aryllithium or arylmagnesium compounds followed by reaction with the appropriate chlorotrialkyltin, or via reaction with the appropriate bis(trialkyltin) and an organometallic catalyst.

The compounds of formula I in which E represents oxygen, sulfur, or $NR^{10}$ may be prepared according to the following methods outlined in Scheme 2.

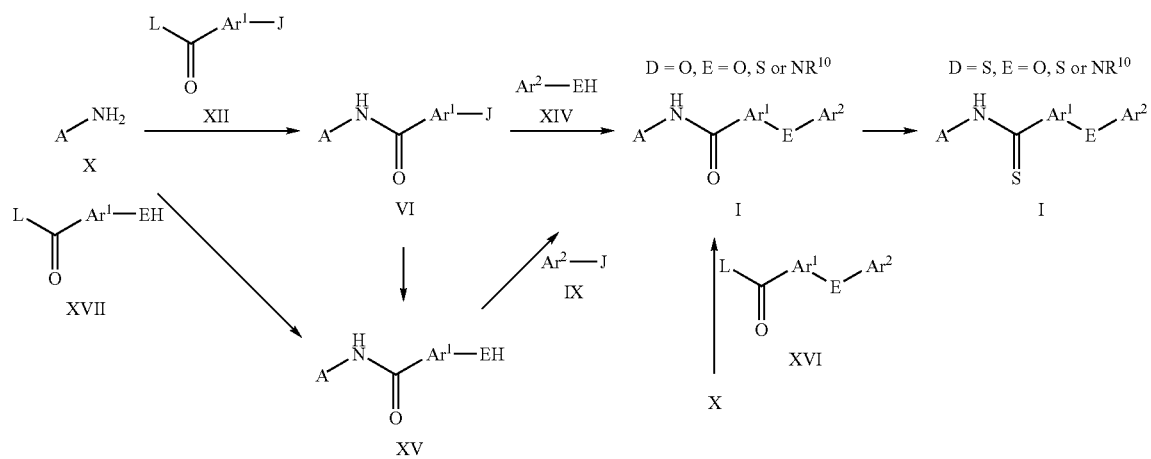

catalyst and solvent. Suitable compounds of formula XIII include boronic acids, in which M represents $B(OH)_2$ and organotin compounds, in which M represents a suitable trialkylstannyl group, for example trimethylstannyl or tri-n-butylstannyl. Suitable organometallic catalysts include palladium (0) complexes, for example tetrakis(triphenylphosphine)palladium (0) or a combination of tris(dibenzylideneacetone)dipalladium (0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula VIII is a boronic acid, the presence of a suitable base in addition to the other reagents is preferred. Suitable bases include sodium carbonate, cesium carbonate, and barium hydroxide. The reaction is carried out at a temperature of 0–120° C., and preferably at a temperature of 60–120° C.

Compounds of formula VII and compounds of formula XIII are either commercially available, or may be prepared by methods known to one skilled in the art. In particular, methods are known to one skilled in the art for the conversion of aryl halides or heteroaryl halides to aryl or heteroaryl boronic acids or aryl or heteroaryl trialkylstannanes, providing methods for the conversion of compounds of formula IX in which J represents halogen to compounds of formula VII and compounds of formula XII in which J represents halogen to compounds of formula XIII. For example, boronic acids may be synthesised from aryl or heteroaryl halides via conversion to the aryllithium or arylmagnesium Compounds of formula I wherein D represents oxygen and E represents $NR^{10}$ may be prepared from compounds of formula VI wherein J represents a halogen or $OSO_2CF_3$ substituent at the position of ring $Ar^1$ at which the bond to nitrogen is formed, by reaction with an appropriate amine of formula XIV in which EH represents $NHR^{10}$. The reaction may be performed by heating in an inert solvent in the presence of a suitable strong base. Suitable inert solvents include ether solvents, for example tetrahydrofuran, 1,4-dioxane, 1,2-dimethoxyethane, or di(2-methoxyethyl)ether, a hydrocarbon solvent, for example benzene or toluene, or an amide solvent, for example dimethylformamide, or N-methyl-2-pyrrolidinone. The preferred solvent is tetrahydrofuran. Suitable strong bases include alkali metal alkoxide or amide bases, for example sodium t-butoxide or potassium t-butoxide, lithium bis(trimethylsilyl)amide, or lithium diisopropylamide. The preferred strong base is sodium t-butoxide. The reaction may require, and is preferably performed in, the presence of an organometallic catalyst. Suitable organometallic catalysts include complexes of palladium (0) with a suitable phosphine ligand, preferably a triarylphosphine ligand, and most preferably a bidentate triarylphosphine ligand. Preferred ligands include 2,2'-bis(diphenylphosphino)-1,1'-binaphthyl or 1,1'-bis(diphenylphosphino)ferrocene. The catalyst may be synthesised by the combination of a suitable source of palladium (0), for example tris(dibenzylideneacetone)dipalladium (0), with the phosphine ligand, and may either be pre-formed or formed in situ by including the palladium source and phophine ligand in the reaction mixture. The reaction is carried out at a temperature of 0–150° C., and preferably at a temperature of 60–120° C.

Compounds of formula I wherein D represents oxygen and E represents $NR^{10}$ may also be prepared from compounds of formula IX wherein J represents a halogen or $OSO_2CF_3$ substituent at the position of ring $Ar^2$ at which the bond to nitrogen is formed, by reaction with an appropriate amine of formula XV in which EH represents $NHR^{10}$. The reaction may be performed by heating in an inert solvent in the presence of a suitable strong base. Suitable inert solvents include ether solvents, for example tetrahydrofuran, 1,4-dioxane, 1,2-dimethoxyethane, or di(2-methoxyethyl)ether, a hydrocarbon solvent, for example benzene or toluene, or an amide solvent, for example dimethylformamide, or N-methyl-2-pyrrolidinone. The preferred solvent is tetrahydrofuran. Suitable strong bases include alkali metal alkoxide or amide bases, for example sodium t-butoxide or potassium t-butoxide, lithium bis(trimethylsilyl)amide, or lithium diisopropylamide. The preferred strong base is sodium t-butoxide. The reaction may require, and is preferably performed in, the presence of an organometallic catalyst. Suitable organometallic catalysts include complexes of palladium (0) with a suitable phosphine ligand, preferably a triarylphosphine ligand, and most preferably a bidentate triarylphosphine ligand. Preferred ligands include 2,2'-bis(diphenylphosphino)-1,1'-binaphthyl or 1,1'-bis(diphenylphosphino)ferrocene. The catalyst may be synthesised by the combination of a suitable source of palladium (0), for example tris(dibenzylideneacetone)dipalladium (0), with the phosphine ligand, and may either be pre-formed or formed in situ by including the palladium source and phophine ligand in the reaction mixture. The reaction is carried out at a temperature of 0–150° C., and preferably at a temperature of 60–120° C.

Compounds of formula I wherein D represents oxygen and E represents oxygen or sulfur may be prepared from compounds of formula VI wherein J represents a halogen or $OSO_2CF_3$ substituent at the position of ring $Ar^1$ at which the bond to oxygen is formed, by reaction with an appropriate compound of formula XIV in which EH represents OH or SH. The reaction may be performed by heating in an inert solvent in the presence of a suitable base. The reaction may require, and is preferably performed in, the presence of a catalyst. Suitable inert solvents include ether solvents, for example tetrahydrofuran, 1,4-dioxane, 1,2-dimethoxyethane, or di(2-methoxyethyl)ether, an amide solvent, for example dimethylformamide, or N-methyl-2-pyrrolidinone, or a basic heterocyclic aromatic solvent, for example pyridine. The preferred solvent is pyridine. Suitable bases include alkali metal alkoxides, or alkali metal carbonates, for example potassium carbonate. Suitable organometallic catalysts include copper or its salts, preferably copper (I) salts, and most preferably copper (I) iodide. The reaction is carried out at a temperature of 0–150° C., and preferably at a temperature of 100–150° C.

Compounds of formula I wherein D represents oxygen and E represents oxygen or sulfur may also be prepared from compounds of formula IX wherein J represents a halogen or $OSO_2CF_3$ substituent at the position of ring $Ar^2$ at which the bond to nitrogen is formed, by reaction with an appropriate compound of formula XV in which EH represents OH or SH. The reaction may be performed by heating in an inert solvent in the presence of a suitable base. The reaction may require, and is preferably performed in, the presence of a catalyst. Suitable inert solvents include ether solvents, for example tetrahydrofuran, 1,4-dioxane, 1,2-dimethoxyethane, or di(2-methoxyethyl)ether, an amide solvent, for example N,N-dimethylformamide, or N-methylpyrrolidinone, or a basic heterocyclic aromatic solvent, for example pyridine. The preferred solvent is pyridine. Suitable bases include alkali metal alkoxides, or alkali metal carbonates, for example potassium carbonate. Suitable organometallic catalysts include copper or its salts, preferably copper (I) salts, and most preferably copper (I) iodide. The reaction is carried out at a temperature of 0–150° C., and preferably at a temperature of 100–150° C.

Compounds of formula I wherein D represents oxygen and E represents oxygen, sulfur, or $NR^{10}$ may also be prepared from compounds of formula X by reaction with a suitable compound of formula XVI, wherein E represents oxygen, sulfur, or $NR^{10}$ and L represents a suitable leaving group, using a suitable acylation procedure. Suitable leaving groups L include: OH, halogen, OAlkyl, OAryl, OCOAlkyl, OCOAryl. A suitable acylation procedure involves treatment of a compound of formula X with a compound of formula XI at 0–120° C. in a suitable solvent. The presence of a base, or, when Y=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when L=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tet-rahydrofuran, or chloroform. The preferred solvent is N,N-dimethylformamide. The reaction is preferably performed at a temperature of 0–50° C., and most preferably at a temperature of 20–30° C.

Compounds of formula XV wherein EH represents OH, SH, or $NHR^{10}$ may be prepared from compounds of formula X by reaction with a suitable compound of formula XVII, wherein L represents a suitable leaving group and EH represents OH, SH or $NHR^{10}$, using a suitable acylation procedure. Suitable leaving groups L include: OH, halogen, OAlkyl, OAryl, OCOAlkyl, OCOAryl. A suitable acylation procedure involves treatment of a compound of formula X with a compound of formula XVII at 0–120° C. in a suitable solvent. The presence of a base, or, when L=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when L=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0–50° C., and most preferably at a temperature of 20–30° C.

Compounds of formula I, XIV, XV or XVII in which E represents $NR^{10}$ and $R^{10}$ represents an alkyl group may be prepared from compounds of the corresponding formula wherein $R^{10}$ represents hydrogen by a suitable alkylation procedure. Typical alkylation procedures include treatment with an appropriate alkyl halide or sulfonate ester and base, for example sodium hydride, in a suitable solvent, for example N,N-dimethylformamide, or reductive alkylation using the appropriate aldehyde or ketone together with a suitable reducing agent in the presence of an acidic catalyst and in an inert solvent. The preferred method is reductive alkylation. Suitable reducing agents include sodium borohydride and sodium cyanoborohydride. The preferred reducing agent is sodium borohydride. Suitable inert solvents include water, methanol or ethanol. The preferred solvent is methanol. Suitable acidic catalysts include acetic acid or zinc chloride. The preferred acidic catalyst is acetic acid. The reaction is usually conducted at a temperature of 0–100° C., and preferably at 20–65° C.

Compounds of formula I, XIV, XV or XVII in which E represents $NR^{10}$ and $R^{10}$ represents an aryl or heteroaryl group may be prepared from compounds of the corresponding formula wherein $R^{10}$ represents hydrogen by reaction with an appropriate aromatic or heteroaromatic halide or trifluoromethanesulfonate. The reaction may be performed by heating in an inert solvent in the presence of a suitable strong base. Suitable inert solvents include ether solvents, for example tetrahydrofuran, 1,4-dioxane, 1,2-dimethoxyethane, or di(2-methoxyethyl)ether, a hydrocarbon solvent, for example benzene or toluene, or an amide solvent, for example N,N-dimethylformamide, or N-methyl-2-pyrrolidinone. The preferred solvent is tetrahydrofuran. Suitable strong bases include alkali metal alkoxide or amide bases, for example sodium t-butoxide or potassium t-butoxide, lithium bis(trimethylsilyl)amide, or lithium diisopropylamide. The preferred strong base is sodium t-butoxide. The reaction may require, and is preferably performed in, the presence of an organometallic catalyst. Suitable organometallic catalysts include complexes of palladium (0) with a suitable phosphine ligand, preferably a triarylphosphine ligand, and most preferably a bidentate triarylphosphine ligand. Preferred ligands include 2,2'-bis(diphenylphosphino)-1,1'-binaphthyl or 1,1'-bis(diphenylphosphino)ferrocene. The catalyst may be synthesised by the combination of a suitable source of palladium (0), for example tris(dibenzylideneacetone)dipalladium (0), with the phosphine ligand, and may either be preformed or formed in situ by including the palladium source and phophine ligand in the reaction mixture. The reaction is carried out at a temperature of 0–150° C., and preferably at a temperature of 60–120° C.

Compounds of formula I in which D represents sulfur and E represents oxygen or $NR^{10}$ may be prepared from compounds of formula I in which D represents oxygen and E represents oxygen, or $NR^{10}$ by reaction with a suitable sulfide in a suitable solvent. The preferred sulfides are phosphorus sulfides, in particular 4-methoxyphenylthionophosphine sulfide dimer ("Lawesson's Reagent"), and diphosphorus pentasulfide. Suitable solvents for the reaction include aryl hydrocarbon solvents, for example toluene or xylene. The reaction is performed at a temperature of 0–200° C., and preferably at a temperature of 50–180° C.

Compounds of formula XVI wherein D represents oxygen and E represents $NR^{10}$ may be prepared from compounds of formula XII wherein J represents a halogen or $OSO_2CF_3$ substituent at the position of ring $Ar^1$ at which the bond to nitrogen is formed, by reaction with an appropriate amine of formula XIV in which EH represents $NHR^{10}$, or, alternatively, from compounds of formula XVII in which EH represents $NHR^{10}$ by reaction with an appropriate compound of formula IX wherein J represents a halogen or $OSO_2CF_3$ substituent at the position of ring $Ar^2$ at which the bond to nitrogen is formed. The reaction may be performed by heating in an inert solvent in the presence of a suitable strong base. Suitable inert solvents include ether solvents, for example tetrahydrofuran, 1,4-dioxane, 1,2-dimethoxyethane, or di(2-methoxyethyl)ether, a hydrocarbon solvent, for example benzene or toluene, or an amide solvent, for example N,N-dimethylformamide, or N-methyl-2-pyrrolidinone. The preferred solvent is tetrahydrofuran. Suitable strong bases include alkali metal alkoxide or amide bases, for example sodium t-butoxide or potassium t-butoxide, lithium bis(trimethylsilyl)amide, or lithium diisopropylamide. The preferred strong base is sodium t-butoxide. The reaction may require, and is preferably performed in, the presence of an organometallic catalyst. Suitable organometallic catalysts include complexes of palladium (0) with a suitable phosphine ligand, preferably a triarylphosphine ligand, and most preferably a bidentate triarylphosphine ligand. Preferred ligands include 2,2'-bis(diphenylphosphino)-1,1'-binaphthyl or 1,1'-bis(diphenylphosphino)ferrocene. The catalyst may be synthesised by the combination of a suitable source of palladium (0), for example tris(dibenzylideneacetone)dipalladium (0), with the phosphine ligand, and may either be pre-formed or formed in situ by including the palladium source and phophine ligand in the reaction mixture. The reaction is carried out at a temperature of 0–150° C., and preferably at a temperature of 60–120° C.

Compounds of formula XVI wherein D represents oxygen and E represents oxygen or sulfur may be prepared from compounds of formula XII wherein J represents a halogen or $OSO_2CF_3$ substituent at the position of ring $Ar^1$ at which the bond to oxygen or sulfur is formed, by reaction with an appropriate compound of formula XIV in which EH represents OH or SH, or, alternatively, from compounds of formula XVII in which EH represents OH or SH by reaction with an appropriate compound of formula IX wherein J represents a halogen or $OSO_2CF_3$ substituent at the position of ring $Ar^2$ at which the bond to oxygen or sulfur is formed. The reaction may be performed by heating in an inert solvent in the presence of a suitable base. The reaction may require, and is preferably performed in, the presence of a catalyst. Suitable inert solvents include ether solvents, for example tetrahydrofuran, 1,4-dioxane, 1,2-dimethoxyethane, or di(2-methoxyethyl)ether, an amide solvent, for example N,N-dimethylformamide, or N-methyl-2-pyrrolidinone, or a basic heterocyclic aromatic solvent, for example pyridine. The preferred solvent is pyridine. Suitable bases include alkali metal alkoxides, or alkali metal carbonates, for example potassium carbonate. Suitable organometallic catalysts include copper or its salts, preferably copper (I) salts, and most preferably copper (I) iodide. The reaction is carried out at a temperature of 0–150° C., and preferably at a temperature of 100–150° C.

Compounds of formula IX, X, and XII, XIV, and XVII are either commercially available, known in the literature, or may be prepared by methods known to one skilled in the art.

It will be appreciated by one skilled in the art that certain optional aromatic substituents in the compounds of the invention may be introduced by employing aromatic substitution reactions, or functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalisation of an aromatic ring, for example via nitration, halogenation, or acylation; transformation of a nitro group to an amino group, for example via reduction, such as by catalytic hydrogenation; acylation, alkylation, sulfonylation of an amino or hydroxyl group; replacement of an amino group by another functional group via conversion to an intermediate diazonium salt followed by nucleophilic or free radical substitution of the diazonium salt; or replacement of a halogen by another functional group, for example via nucleophilic or organometallically-catalysed substitution reactions.

Where necessary, hydroxy, amino, or other reactive groups may be protected using a protecting group as described in the standard text "Protecting groups in Organic Synthesis", $3^{rd}$ Edition (1999) by Greene and Wuts.

The above described reactions, unless otherwise noted, are usually conducted at a pressure of about one to about three atmospheres, preferably at ambient pressure (about one atmosphere).

Unless otherwise stated, the above described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions which will not cause racemisation.

Intermediates

A further aspect of the invention relates to intermediates. Of interest among the intermediates are compounds of formula VI in Scheme 1. These intermediates are useful in the synthesis of compounds of formula I, but their use is not limited to the synthesis of such compounds. For example, compounds of formula VI are active as ligands for acetylcholine receptors, and therefore share the utilities described for compounds of formula I.

Accordingly, there is also provided a compound of formula VI:

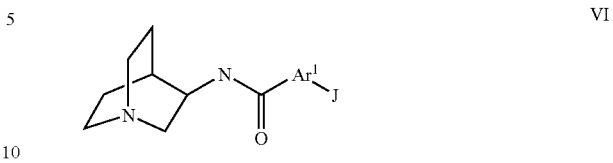

VI wherein:
Ar$^1$ represents a benzene, furan, or thiophene ring;
J represents halogen, or $OSO_2CF_3$, provided that when Ar$^1$ represents a benzene ring, J may only represent bromine, iodine, or $OSO_2CF_3$ in a position meta or para to the carboxamide group; or an enantiomer thereof and pharmaceutically-acceptable salts thereof.

Preferred compounds of this aspect of the invention include the following:
N-(1-Azabicyclo[2.2.2]oct-3-yl)(5-bromofuran-2-carboxamide);
N-(1-Azabicyclo[2.2.2]oct-3-yl)(5-bromothiophene-2-carboxamide);
N-(1-Azabicyclo[2.2.2]oct-3-yl)(3-bromobenzamide);
N-(1-Azabicyclo[2.2.2]oct-3-yl)(4-bromobenzamide);
N-(1-Azabicyclo[2.2.2]oct-3-yl)(3-iodobenzamide);
N-(1-Azabicyclo[2.2.2]oct-3-yl)(4-iodobenzamide);
N-(1-Azabicyclo[2.2.2]oct-3-yl)(4-bromothiophene-2-carboxamide);
N-(1-Azabicyclo[2.2.2]oct-3-yl)(5-bromothiophene-3-carboxamide);
or an enantiomer thereof, and pharmaceutically-acceptable salts thereof.

Particularly preferred compounds of this aspect of the invention include the following:
(R)-N-(1-Azabicyclo[2.2.2]oct-3-yl)(5-bromofuran-2-carboxamide);
(R)-N-(1-Azabicyclo[2.2.2]oct-3-yl)(5-bromothiophene-2-carboxamide);
(S)-N-(1-Azabicyclo[2.2.2]oct-3-yl)(5-bromothiophene-2-carboxamide);
(R)-N-(1-Azabicyclo[2.2.2]oct-3-yl)(3-bromobenzamide);
(R)-N-(1-Azabicyclo[2.2.2]oct-3-yl)(4-bromobenzamide);
(R)-N-(1-Azabicyclo[2.2.2]oct-3-yl)(3-iodobenzamide);
(R)-N-(1-Azabicyclo[2.2.2]oct-3-yl)(4-iodobenzamide);
(R)-N-(1-Azabicyclo[2.2.2]oct-3-yl)(4-bromothiophene-2-carboxamide);
(R)-N-(1-Azabicyclo[2.2.2]oct-3-yl)(5-bromothiophene-3-carboxamide);
or an enantiomer thereof, and pharmaceutically-acceptable salts thereof.

Intermediate compounds also exist in enantiomeric forms and may be used as purified enantiomers, racemates or mixtures.

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof or a pharmaceutically-acceptable salt thereof, effective in treating or preventing such disorder or condition in admixture with an inert pharmaceutically-acceptable diluent or carrier.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically-acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically-acceptable diluent or carrier.

Examples of diluents and carriers are:
for tablets and dragees: lactose, starch, talc, stearic acid;
for capsules: tartaric acid or lactose;
for injectable solutions: water, alcohols, glycerin, vegetable oils;
for suppositories: natural or hardened oils or waxes.

There is also provided a process for the preparation of such a pharmaceutical composition which comprises mixing the ingredients.

Utility

A further aspect of the invention is the use of a compound according to the invention, an enantiomer thereof or a pharmaceutically-acceptable salt thereof, in the manufacture of a medicament for the treatment or prophylaxis of one of the below mentioned diseases or conditions; and a method of treatment or prophylaxis of one of the above mentioned diseases or conditions, which comprises administering a therapeutically effective amount of a compound according to the invention, or an enantiomer thereof or a pharmaceutically-acceptable salt thereof, to a patient.

Compounds according to the invention are agonists of nicotinic acetylcholine receptors. While not being limited by theory, it is believed that agonists of the $\alpha_7$ nAChR (nicotinic acetylcholine receptor) subtype should be useful in the treatment or prophylaxis of psychotic disorders and intellectual impairment disorders, and have advantages over compounds which are or are also agonists of the $\alpha_4$ nAChR subtype. Therefore, compounds which are selective for the $\alpha_7$ nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, Lewy Body Dementia, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for Affinity at $\alpha_7$ nAChR Subtype

125I-$\alpha$-Bungarotoxin (BTX) binding to rat hippocampal membranes. Rat hippocampi were homogenized in 20 volumes of cold homogenisation buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and re-suspended in HB. Membranes (30–80 µg) were incubated with 5 nM [125I] $\alpha$-BTX, 1 mg/mL BSA (bovine serum albumin), test drug, and either 2 mM $CaCl_2$ or 0.5 mM EGTA [ethylene glycol-bis($\beta$-aminoethylether)] for 2 hours at 21° C., and then filtered and washed 4 times over Whatman glass fibre filters (thickness C) using a Brandel cell harvester. Pre-treating the filters for 3 hours with 1% (BSA/0.01% PEI (polyethyleneimine) in water was critical for low filter blanks (0.07% of total counts per minute). Non-specific binding was described by 100 µM (−)-nicotine, and specific binding was typically 75%.

Test B—Assay for Affinity to the $\alpha_4$ nAChR Subtype

[$_3$H]-(−)-nicotine binding. Using a procedure modified from Martino-Barrows and Kellar (Mol Pharm (1987) 31:169–174), rat brain (cortex and hippocampus) was homogenised as in the [$_{125}$I] $\alpha$-BTX binding assay, centrifuged for 20 minutes at 12,000×g, washed twice, and then re-suspended in HB containing 100 µM diisopropyl fluorophosphate. After 20 minutes at 4° C., membranes (approximately 0.5 mg) were incubated with 3 nM [3H]-(−)-nicotine, test drug, 1 µM atropine, and either 2 mM $CaCl_2$ or 0.5 mM EGTA for 1 hour at 4° C., and then filtered over Whatman glass fibre filters (thickness C) (pre-treated for 1 hour with 0.5% PEI) using a Brandel cell harvester. Non-specific binding was described by 100 µM carbachol, and specific binding was typically 84%.

Binding Data Analysis for Tests A and B $IC_{50}$ values and pseudo Hill coefficients (nH) were calculated using the non-linear curve fitting program ALLFIT (DeLean A, Munson P J and Rodbard D (1977) Am. J. Physiol., 235:E97–E102). Saturation curves were fitted to a one site model, using the non-linear regression program ENZFITTER (Leatherbarrow, R. J. (1987)), yielding $K_D$ values of 1.67 and 1.70 nM for the 125I-$\alpha$-BTX and [3H]-(−)-nicotine ligands respectively. $K_i$ values were estimated using the general Cheng-Prusoff equation:

$$K_i = [IC_{50}]/((2+([\text{ligand}]/K_D)^n)^{1/n} - 1)$$

where a value of n=1 was used whenever $n_H$<1.5 and a value of n=2 was used when $n_H \geq 1.5$. Samples were assayed in triplicate and were typically ±5%. $K_i$ values were determined using 6 or more drug concentrations. The compounds of the invention are compounds with binding affinities ($K_i$) of less than 10 µM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

General Experimental Procedures

Commercial reagents were used without further purification. Mass spectra were recorded using either a Hewlett Packard 5988A or a MicroMass Quattro-1 Mass Spectrometer and are reported as m/z for the parent molecular ion. Room temperature refers to 20–25° C.

EXAMPLES

The following examples are preferred non-limiting examples embodying preferred aspects of the invention.

Intermediate 1

(R)-N-(1-Azabicyclo[2.2.2]oct-3-yl)(5-bromofuran-2-carboxamide)

A mixture of (R)-1-azabicyclo[2.2.2]oct-3-ylamine dihydrochloride (655 mg), 5-bromofuran-2-carboxylic acid (681 mg), 1-hydroxybenzotriazole hydrate (457 mg), O-benzotriazol-1-yl-N,N,N',N'-tetramethyluronium tetrafluoroborate (1.069 g), and N,N-diisopropylethylamine (2.5 mL) in N,N-dimethylformamide (10 mL) was agitated until a homogenous solution was obtained, and was then allowed to stand at room temperature overnight. The solution was evaporated, and the residue was partitioned between aqueous sodium hydroxide and chloroform. The chloroform layer was dried over magnesium sulfate, filtered, and evaporated and the residue was purified by chromatography on silica gel in a solid phase extraction cartridge using ammoniated methanol/chloroform mixtures as the eluent. The compound was then dissolved in tetrahydrofuran (20 mL), excess hydrogen chloride (5 mL; 1M solution in diethyl ether) was added, and the solution was evaporated and then recrystallised from methanol/diethyl ether to give the hydrochloride salt of the title compound as a colourless solid (538 mg); MS (ES$^+$) 299, 301 (MH$^+$).

Intermediate 2

(R)-N-(1-Azabicyclo[2.2.2]oct-3-yl)(5-bromothiophene-2-carboxamide)

A mixture of (R)-1-azabicyclo[2.2.2]oct-3-ylamine dihydrochloride (4 g), 5-bromothiophene-2-carboxylic acid (4.25 g), 1-hydroxybenzotriazole hydrate (2.77 g), O-benzotriazol-1-yl-N,N,N',N'-tetramethyluronium tetrafluoroborate (6.6 g), and N,N-diisopropylethylamine (14 mL), in N,N-dimethylformamide (100 mL) was stirred at room temperature overnight. The solution was evaporated, and the residue was partitioned between aqueous sodium hydroxide and chloroform. The chloroform layer was dried over magnesium sulfate, filtered, and evaporated. The residue was purified by flash chromatography on silica gel and eluted with 5%–20% 3.5N methanolic ammonia/chloroform mixtures. Evaporation of solvent gave yellow solid (5.87 g); MS (ES$^+$) 315, 317 (MH$^+$).

Intermediate 3

(S)-N-(1-Azabicyclo[2.2.2]oct-3-yl)(5-bromothiophene-2-carboxamide)

A mixture of (S)-N-1-azabicyclo[2.2.2]oct-3-ylamine dihydrochloride (1.9 g), 5-bromothiophene-2-carboxylic acid (1.97 g), 1-hydroxybenzotriazole hydrate (1.28 g), O-benzotriazol-1-yl-N,N,N',N'-tetramethyluronium tetrafluoroborate (3.06 g), and N,N-diisopropylethylamine (8.3 mL) in N,N-dimethylformamide (20 mL) was stirred at room temperature overnight. The solution was evaporated, and the residue was partitioned between aqueous sodium hydroxide and chloroform. The chloroform layer was dried (Mg$_2$SO$_4$), filtered, and evaporated. The residue was purified by flash chromatography on silica gel and eluted with 5%–20% 3.5M methanolic ammonia/chloroform mixtures. Evaporation of solvent gave white solid (3 g); MS (ES$^+$) 315, 317 (MH$^+$).

Intermediate 4

(R)-N-(1-Azabicyclo[2.2.2]oct-3-yl)(3-bromobenzamide)

Prepared by a method analogous to that described for the preparation of Intermediate 1 from (R)-1-azabicyclo[2.2.2]oct-3-ylamine dihydrochloride and 3-bromobenzoic acid; the compound was purified by chromatography on silica gel using ammoniated methanol/chloroform mixtures as the eluent. The compound was then dissolved in tetrahydrofuran, excess hydrogen chloride (1M solution in diethyl ether) was added, and the solution was evaporated and then recrystallised from methanol/diethyl ether to give the hydrochloride salt of the title compound as a colourless solid; MS (ES$^+$) 309, 311 (MH$^+$).

Intermediate 5

(R)-N-(1-Azabicyclo[2.2.2]oct-3-yl)(4-bromobenzamide)

Prepared by a method analogous to that described for the preparation of Intermediate I from (R)-1-azabicyclo[2.2.2]oct-3-ylamine dihydrochloride and 4-bromobenzoic acid; the compound was purified by chromatography on silica gel using ammoniated methanol/chloroform mixtures as the eluent. The compound was then dissolved in tetrahydrofuran, excess hydrogen chloride (1M solution in diethyl ether) was added, and the solution was evaporated and then recrystallised from methanol/t-butyl methyl ether to give the hydrochloride salt of the title compound as a colourless solid; MS (ES$^+$) 309, 311 (MH$^+$).

Intermediate 6

(R)-N-(1-Azabicyclo[2.2.2]oct-3-yl)(3-iodobenzamide)

Prepared by a method analogous to that described for the preparation of Intermediate 1 from (R)-1-azabicyclo[2.2.2]oct-3-ylamine dihydrochloride and 3-iodobenzoic acid; the compound was purified by solid phase extraction on silica gel using ammoniated methanol/chloroform mixtures as the eluent followed by reverse phase HPLC on a Waters Bondapak® C$_{18}$ column using a gradient of acetonitrile and 0.1% aqueous trifluoroacetic acid as the eluent. The product-containing fractions were evaporated, the residue was dissolved in methanol, excess hydrogen chloride solution (4M in 1,4-dioxane) was added and the solution was evaporated to give the hydrochloride salt of the title compound as a colourless solid; MS (ES$^+$) 357 (MH$^+$).

Intermediate 7

(R)-N-(1-Azabicyclo[2.2.2]oct-3-yl)(4-iodobenzamide)

Prepared by a method analogous to that described for the preparation of Intermediate 1 from (R)-1-azabicyclo[2.2.2]oct-3-ylamine dihydrochloride and 4-iodobenzoic acid; the compound was purified by solid phase extraction on silica gel using ammoniated methanol/chloroform mixtures as the eluent followed by reverse phase HPLC on a Waters Bondapak® C$_{18}$ column using a gradient of acetonitrile and 0.1% aqueous trifluoroacetic acid as the eluent. The product-containing fractions were evaporated, the residue was dissolved in methanol, excess hydrogen chloride solution (4M in 1,4-dioxane) was added and the solution was evaporated to give the hydrochloride salt of the title compound as a colourless solid; MS (ES$^+$) 357 (MH$^+$).

Intermediate 8

(R)-N-(1-Azabicyclo[2.2.2]oct-3-yl)(4-bromothiophene-2-carboxamide)

(A) 4-Bromothiophene-2-carboxylic acid

Chromium (VI) oxide (20 g), and concentrated sulfuric acid (32 g) were dissolved in water (50 mL) and when dissolution was complete, the volume was made up to 100 mL with water. 55 mL of the resulting solution was added dropwise to a solution of 4-bromothiophene-2-carboxaldehyde (19.1 g) in acetone (200 mL) stirred at 0° C. After 2 h, the solution was diluted with water and extracted with chloroform. The organic extracts were washed with water, then extracted with aqueous sodium hydroxide. The alkaline mixture was acidified by cautious addition of concentrated hydrochloric acid then extracted with chloroform. The organic layer was then dried (Mg$_2$SO$_4$), filtered, and evaporated. The resulting solid was recrystallised from diethyl ether/hexane to give a colourless solid; MS (ES$^+$) 207, 209 (MH$^+$).

(B) (R)-N-(1-Azabicyclo[2.2.2]oct-3-yl)(4-bromothiophene-2-carboxamide)

Prepared by a method analogous to that described for the preparation of Intermediate 1 from (R)-1-azabicyclo[2.2.2]oct-3-ylamine dihydrochloride and 4-bromothiophene-2-carboxylic acid. The residue from evaporation of the reaction mixture was partitioned between aqueous hydrochloric acid and chloroform. The aqueous layer was then basified with aqueous sodium hydroxide and extracted with chloroform. The organic extracts were dried (MgSO$_4$), filtered, and evaporated and resulting solid was recrystallised from ethyl acetate/hexane to give the title compound as a colourless solid; MS (ES$^+$) 315, 317 (MH$^+$).

Intermediate 9

(R)-N-(1-Azabicyclo[2.2.2]oct-3-yl)(5-bromothiophene-3-carboxamide)

(A) 5-Bromothiophene-3-carboxylic acid

Bromine (46.5 g) in acetic acid (200 mL) was added dropwise to a solution of thiophene-3-carboxylic acid (38 g) in acetic acid (300 mL). After the addition was complete, stirring was continued at room temperature for 30 min. The reaction mixture was poured into 2000 mL of ice/water and the precipitated solid was collected and recrystallised from water to give a colourless solid; MS (ES$^-$) 205, 207 (MH$^+$).

(B) (R)-N-(1-Azabicyclo[2.2.2]oct-3-yl)(5-bromothiophene-3-carboxamide)

Prepared by a method analogous to that described for the preparation of Intermediate 1 from (R)-1-azabicyclo[2.2.2]oct-3-ylamine dihydrochloride and 5-bromothiophene-3-carboxylic acid. The compound was purified by reverse phase HPLC on a Waters Bondapak® C$_{18}$ column using a gradient of acetonitrile and 0.1% aqueous trifluoroacetic acid as the eluent. The product-containing fractions were evaporated, the residues dissolved in methanol, excess hydrogen chloride solution (4M in 1,4-dioxane) was added and the solution was evaporated. After drying under vacuum, the hydrochloride salt of the title compound was obtained as a colourless solid; MS (ES$^+$) 315, 317 (MH$^+$).

Example 1

(R)-N-(1-Azabicyclo[2.2.2]oct-3-yl)(5-phenylfuran-2-carboxamide)

(R)-N-(1-Azabicyclo[2.2.2]oct-3-yl)(5-bromofuran-2-carboxamide) hydrochloride (100 mg), phenylboronic acid (45 mg), tetrakis(triphenylphosphine)palladium(0) (20 mg), cesium carbonate (547 mg), in a mixture of 1,2-dimethoxyethane (6 mL), ethanol (1.5 mL) and water (1 mL) were stirred under reflux under a nitrogen atmosphere for 17 h. The solution was evaporated and the residue was dissolved in chloroform. The solution was washed with aqueous sodium carbonate and the organic layer was then dried (Mg$_2$SO$_4$), filtered, and evaporated. HPLC purification using a gradient of 1:1 ammoniated methanol in chloroform, and chloroform gave the title compound as a colourless solid (63 mg); MS (ES$^+$) 297 (MH$^+$).

Example 2

(R)-N-(1-Azabicyclo[2.2.2]oct-3-yl)(5-(3-fluorophenyl)furan-2-carboxamide)

Prepared by a method analogous to that described in Example 1 from (R)-N-(1-azabicyclo[2.2.2]oct-3-yl)(5-bromofuran-2-carboxamide) and 3-fluorobenzeneboronic acid, using tetrakis(triphenylphosphine)palladium(0) and sodium carbonate in a mixture of 1,2-dimethoxyethane and water. The compound was purified by filtration through a silica gel solid phase extraction cartridge using ammoniated methanol/chloroform mixtures as the eluent, and then by reverse phase HPLC on a Waters Bondapak® C$_{18}$ column using a gradient of acetonitrile and 0.1% aqueous trifluoroacetic acid as the eluent. Evaporation of solvent gave the trifluoroacetate salt of the title compound as a colourless solid; MS (ES$^+$) 315 (MH$^+$).

Example 3

(R)-N-(1-Azabicyclo[2.2.2]oct-3-yl)(3-(3-thienyl)benzamide)

Prepared by a method analogous to that described in Example 1 from (R)-1-azabicyclo[2.2.2]oct-3-yl)(3-bromobenzamide) and 3-thiopheneboronic acid, using tetrakis(triphenylphosphine)palladium (0) and sodium carbonate in a mixture of tetrahydrofuran, ethanol, and water. The compound was purified by reverse phase HPLC on a Waters Bondapak® C$_{18}$ column using a gradient of acetonitrile and 0.1% aqueous trifluoroacetic acid as the eluent. Evaporation of solvent gave the trifluoroacetate of the title compound as a colourless solid; MS (ES$^+$) 313 (MH$^+$).

Example 4

(R)-N-(1-Azabicyclo[2.2.2]oct-3-yl)(3-phenylbenzamide)

Prepared by a method analogous to that described in Example 1 from (R)-1-azabicyclo[2.2.2]oct-3-yl)(3-bromobenzamide) and phenylboronic acid, using tetrakis(triphenylphosphine)palladium(0) and sodium carbonate in a mixture of tetrahydrofuran, ethanol, and water. The compound was purified by flash chromatography on silica gel and eluted with 3%–10% 3.5N methanolic ammonia/chloroform mixtures. Evaporation of solvent gave the title compound as a colourless solid; MS (ES$^+$) 307 (MH$^+$).

Example 5

(R)-N-(1-Azabicyclo[2.2.2]oct-3-yl)(3-(3-pyridyl)benzamide)

Prepared by a method analogous to that described in Example 1 from (R)-1-azabicyclo[2.2.2]oct-3-yl)(3-bromobenzamide) and pyridine-3-boronic acid, using tetrakis(triphenylphosphine)palladium(0) and sodium carbonate in a mixture of tetrahydrofuran, ethanol, and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a colourless solid; MS (ES$^+$) 308 (MH$^+$).

Example 6

(R)-N-(1-Azabicyclo[2.2.2]oct-3-yl)(5-phenylthiophene-2-carboxamide)

Prepared by a method analogous to that described in Example 1 from (R)-N-(1-azabicyclo[2.2.2]oct-3-yl)(5-bromothiophene-2-carboxamide) and phenylboronic acid, using tetrakis(triphenylphosphine)palladium(0) and sodium carbonate in a mixture of tetrahydrofuran, ethanol, and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 313 (MH$^+$).

Example 7

(R)-N-(1-Azabicyclo[2.2.2]oct-3-yl)(3-(3-methoxyphenyl)benzamide)

Prepared by a method analogous to that described in Example 1 from (R)-N-(1-azabicyclo[2.2.2]oct-3-yl)(3-bromobenzamide) and 3-methoxyphenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 337 (MH$^+$).

Example 8

(R)-N-(1-Azabicyclo[2.2.2]oct-3-yl)(3-(2-methoxyphenyl)benzamide)

Prepared by a method analogous to that described in Example 1 from (R)-N-(1-azabicyclo[2.2.2]oct-3-yl)(3-bromobenzamide) and 2-methoxyphenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 337 (MH$^+$).

Example 9

(R)-N-(1-Azabicyclo[2.2.2]oct-3-yl)(3-(3-(N-acetylamino)phenyl)benzamide)

Prepared by a method analogous to that described in Example 1 from (R)-N-(1-azabicyclo[2.2.2]oct-3-yl)(3-bromobenzamide) and 3-(N-acetylamino)phenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 364 (MH$^+$).

Example 10

(R)-N-(1-Azabicyclo[2.2.2]oct-3-yl)(3-(3-fluorophenyl)benzamide)

Prepared by a method analogous to that described in Example 1 from (R)-N-(1-azabicyclo[2.2.2]oct-3-yl)(3-bromobenzamide) and 3-fluorobenzeneboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 325 (MH$^+$).

Example 11

(R)-N-(1-Azabicyclo[2.2.2]oct-3-yl)(3-(3-methylphenyl)benzamide)

Prepared by a method analogous to that described in Example 1 from (R)-N-(1-azabicyclo[2.2.2]oct-3-yl)(3-bromobenzamide) and 3-methylphenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 321(MH$^+$).

Example 12

(R)-N-(1-Azabicyclo[2.2.2]oct-3-yl)(3-(2-thienyl)benzamide)

Prepared by a method analogous to that described in Example 1 from (R)-N-(1-azabicyclo[2.2.2]oct-3-yl)(3-bromobenzamide) and 2-thiopheneboronic acid, using tetrakis(triphenylphosphine)palladium(0), cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) (MH$^+$).

Example 13

(R)-N-(1-Azabicyclo[2.2.2]oct-3-yl)(3-(3,5-dichlorophenyl)benzamide)

Prepared by a method analogous to that described in Example 1 from (R)-N-(1-azabicyclo[2.2.2]oct-3-yl)(3-bromobenzamide) and 3,5-dichlorophenylboronic acid, tetrakis(triphenylphosphine)palladium(0), cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 375,377 MH$^+$).

Example 14

(R)-N-(1-Azabicyclo[2.2.2]oct-3-yl)(3-(2-naphthyl)benzamide)

Prepared by a method analogous to that described in Example 1 from (R)-N-(1-azabicyclo[2.2.2]oct-3-yl)(3-bromobenzamide) and 2-naphthaleneboronic acid, tetrakis(triphenylphosphine)palladium(0), cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 357 (MH$^+$).

Example 15

(R)-N-(1-Azabicyclo[2.2.2]oct-3-yl)(3-(4-fluorophenyl)benzamide)

Prepared by a method analogous to that described in Example 1 from (R)-N-(1-azabicyclo[2.2.2]oct-3-yl)(3-bromobenzamide) and 4-fluorophenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 325 (MH$^+$).

Example 16

(R)-N-(1-Azabicyclo[2.2.2]oct-3-yl)(5-(3-pyridyl)furan-2-carboxamide)

Prepared by a method analogous to that described in Example 1 from (R)-N-(1-azabicyclo[2.2.2]oct-3-yl)(5-bromofuran-2-carboxamide) and pyridine-3-boronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a colourless solid; MS (ES$^+$) 298 (MH$^+$).

Example 17

(R)-N-(1-Azabicyclo[2.2.2]oct-3-yl)(5-(3-thienyl)furan-2-carboxamide)

Prepared by a method analogous to that described in Example 1 from (R)-N-(1-azabicyclo[2.2.2]oct-3-yl)(5-bromofuran-2-carboxamide) and 3-thiopheneboronic acid, tetrakis(triphenylphosphine)palladium(0), sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 303(MH$^+$).

Example 18

(R)-N-(1-Azabicyclo[2.2.2]oct-3-yl)(5-(2-benzo[b]furanyl)furan-2-carboxamide)

Prepared by a method analogous to that described in Example 1 from (R)-N-(1-azabicyclo[2.2.2]oct-3-yl)(5-bromofuran-2-carboxamide) and benzo[b]furan-2-boronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 337 (MH$^+$).

Example 19

(R)-N-(1-Azabicyclo[2.2.2]oct-3-yl)(5-(4-pyridyl)furan-2-carboxamide)

Prepared by a method analogous to that described in Example 1 from (R)-N-(1-azabicyclo[2.2.2]oct-3-yl)(5-bromofuran-2-carboxamide) and pyridine-4-boronic acid, using tetrakis(triphenylphosphine)palladium(0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a colourless solid; MS (ES$^+$) 298 (MH$^+$).

Example 20

(R)-N-(1-Azabicyclo[2.2.2]oct-3-yl)(5-(2-thienyl)furan-2-carboxamide)

Prepared by a method analogous to that described in Example 1 from (R)-N-(1-azabicyclo[2.2.2]oct-3-yl)(5-bromofuran-2-carboxamide) and 2-thiopheneboronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of aceto-

Example 21

(R)-N-(1-Azabicyclo[2.2.2]oct-3-yl)(5-(3-methoxyphenyl)furan-2-carboxamide)

Prepared by a method analogous to that described in Example 1 from (R)-N-(1-azabicyclo[2.2.2]oct-3-yl)(5-bromofuran-2-carboxamide) and 3-methoxyphenylboronic acid, using tetrakis(triphenylphosphine)palladium (0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 327 (MH$^+$).

Example 22

(R)-N-(1-Azabicyclo[2.2.2]oct-3-yl)(5-(2-methoxyphenyl)furan-2-carboxamide)

Prepared by a method analogous to that described in Example 1 from (R)-N-(1-azabicyclo[2.2.2]oct-3-yl)(5-bromofuran-2-carboxamide) and 2-methoxyphenylboronic acid, using tetrakis(triphenylphosphine)palladium(0) and sodium carbonate in a mixture of tetrahydrofuran, ethanol and water. The compound was purified by reverse phase HPLC on a Waters Bondapak®) $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 327 (MH$^+$).

Example 23

(R)-N-(1-Azabicyclo[2.2.2]oct-3-yl)(5-(4-fluorophenyl)furan-2-carboxamide)

Prepared by a method analogous to that described in Example 1 from (R)-N-(1-azabicyclo[2.2.2]oct-3-yl)(5-bromofuran-2-carboxamide) and 4-fluorophenylboronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 315 (MH$^+$).

Example 24

(R)-N-(1-Azabicyclo[2.2.2]oct-3-yl)(5-(2-naphthyl)furan-2-carboxamide)

Prepared by a method analogous to that described in Example 1 from (R)-N-(1-azabicyclo[2.2.2]oct-3-yl)(5-bromofuran-2-carboxamide) and 2-naphthaleneboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 347 (MH$^+$).

Example 25

(R)-N-(1-Azabicyclo[2.2.2]oct-3-yl)(5-(3-methylphenyl)furan-2-carboxamide)

Prepared by a method analogous to that described in Example 1 from (R)-N-(1-azabicyclo[2.2.2]oct-3-yl)(5-bromofuran-2-carboxamide) and 3-methylphenylboronic acid, using tetrakis(triphenylphosphine)palladium(0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 311 (MH$^+$).

Example 26

(R)-N-(1-Azabicyclo[2.2.2]oct-3-yl)(5-(3-furyl)furan-2-carboxamide)

Prepared by a method analogous to that described in Example 1 from (R)-N-(1-azabicyclo[2.2.2]oct-3-yl)(5-bromofuran-2-carboxamide) and 3-furanboronic acid, using tetrakis(triphenylphosphine)palladium (0) and cesium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 287 (MH$^+$).

Example 27

(R)-N-(1-Azabicyclo[2.2.2]oct-3-yl)(5-(2-furyl)furan-2-carboxamide)

A mixture of (R)-N-(1-azabicyclo[2.2.2]oct-3-yl)(5-bromofuran-2-carboxamide) (146 mg), 2-(tri-n-butylstannyl)furan (0.15 mL), tris(dibenzylideneacetone)dipalladium(0) (13 mg), lithium chloride (59 mg), and tri(o-tolyl)phosphine (44 mg) in 1,2-dimethoxyethane (2 mL) was stirred under reflux under a nitrogen atmosphere for 5 h. The solution was filtered and evaporated. The compound was purified by filtration through a silica gel solid phase extraction cartridge using ammoniated methanol/chloroform mixtures as the eluent, and then by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid (59 mg); MS (ES$^+$) 287 (MH$^+$).

Example 28

(R)-N-(1-Azabicyclo[2.2.2]oct-3-yl)(5-(2-pyridyl)furan-2-carboxamide)

Prepared by a method analogous to that described in Example 27 from (R)-N-(1-azabicyclo[2.2.2]oct-3-yl)(5-bromofuran-2-carboxamide) and 2-(tri-n-butylstannyl)pyridine. The compound was purified by filtration through a silica gel solid phase extraction cartridge using ammoniated methanol/chloroform mixtures as the eluent, and then by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a light yellow solid; MS (ES$^+$) 298 (MH$^+$).

Example 29

(R)-N-(1-Azabicyclo[2.2.2]oct-3-yl)(5-(4-pyridyl) thiophene-2-carboxamide)

Prepared by a method analogous to that described in Example 1 from (R)-N-(1-azabicyclo[2.2.2]oct-3-yl)(5-bromothiophene-2-carboxamide) and pyridine-4-boronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a colourless solid; MS (ES$^+$) 314 (MH$^+$).

Example 30

(R)-N-(1-Azabicyclo[2.2.2]oct-3-yl)(5-(3-pyridyl) thiophene-2-carboxamide)

Prepared by a method analogous to that described in Example 1 from (R)-N-(1-azabicyclo[2.2.2]oct-3-yl)(5-bromothiophene-2-carboxamide) and pyridine-3-boronic acid, using tetrakis(triphenylphosphine)palladium (0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a colourless solid; MS (ES$^+$) 314 (MH$^+$).

Example 31

(R)-N-(1-Azabicyclo[2.2.2]oct-3-yl)(5-(2-pyridyl) thiophene-2-carboxamide)

Prepared by a method analogous to that described in Example 27 from (R)-N-(1-azabicyclo[2.2.2]oct-3-yl)(5-bromothiophene-2-carboxamide) and 2-(tri-n-butylstannyl) pyridine. The compound was purified by filtration through a silica gel solid phase extraction cartridge using ammoniated methanol/chloroform mixtures as the eluent, and then by reverse phase BPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a light yellow solid; MS (ES$^+$) 314 (MH$^+$).

Example 32

(R)-N-(1-Azabicyclo[2.2.2]oct-3-yl)(4-(2-pyridyl) thiophene-2-carboxamide)

Prepared by a method analogous to that described in Example 27 from (R)-N-(1-azabicyclo[2.2.2]oct-3-yl)(4-bromothiophene-2-carboxamide) and 2-(tri-n-butylstannyl) pyridine. The compound was purified by filtration through a silica gel solid phase extraction cartridge using ammoniated methanol/chloroform mixtures as the eluent, and then by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a light yellow solid; MS (ES$^+$) 314 (MH$^+$).

Example 33

(R)-N-(1-Azabicyclo[2.2.2]oct-3-yl)(4-(4-pyridyl) thiophene-2-carboxamide)

Prepared by a method analogous to that described in Example 1 from (R)-N-(1-azabicyclo[2.2.2]oct-3-yl)(4-bromothiophene-2-carboxamide) and pyridine-4-boronic acid, using tetrakis(triphenylphosphine)palladium(0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the dihydrochloride salt of the title compound was obtained as a colourless solid; MS (ES$^+$) 314 (MH$^+$).

Example 34

(R)-N-(1-Azabicyclo[2.2.2]oct-3-yl)(4-(3-pyridyl) thiophene-2-carboxamide)

Prepared by a method analogous to that described in Example 1 from (R)-N-(1-azabicyclo[2.2.2]oct-3-yl)(4-bromothiophene-2-carboxamide) and pyridine-3-boronic acid, using tetrakis(triphenylphosphine)palladium (0) and sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a colourless solid; MS (ES$^+$) 314 (MH$^+$).

Example 35

(R)-N-(1-Azabicyclo[2.2.2]oct-3-yl)(5-(3-(N-acetylamino) phenyl)furan-2-carboxamide)

Prepared by a method analogous to that described in Example 1 from (R)-N-(1-azabicyclo[2.2.2]oct-3-yl)(5-bromofuran-2-carboxamide) and 3-(N-acetylamino)phenylboronic acid, using tetrakis(triphenylphosphine)palladium (0)

and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the hydrochloride salt of the title compound as a yellow solid; MS (ES$^+$) 354 (MH$^+$).

Example 36

(R)-N-(1-Azabicyclo[2.2.2]oct-3-yl)(5-(3-nitrophenyl)furan-2-carboxamide)

Prepared by a method analogous to that described in Example 1 from (R)-N-(1-azabicyclo[2.2.2]oct-3-yl)(5-bromofuran-2-carboxamide) and 3-nitrophenylboronic acid, using tetrakis(triphenylphosphine)palladium(0) and sodium carbonate in a mixture of ethylene glycol dimethyl ether and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the hydrochloride salt of the title compound as a yellow solid; MS (ES$^+$) 342 (MH$^+$).

Example 37

(R)-N-(1-Azabicyclo[2.2.2]oct-3-yl)(5-(3-trifluoromethylphenyl)furan-2-carboxamide)

Prepared by a method analogous to that described in Example 1 from (R)-N-(1-azabicyclo[2.2.2]oct-3-yl)(5-bromofuran-2-carboxamide) and 3-trifluoromethylphenylboronic acid, using tetrakis(triphenylphosphine)palladium(0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the hydrochloride salt of the title compound was obtained as a colourless solid; MS (ES$^+$) 365 (MH$^+$).

Example 38

(R)-N-(1-Azabicyclo[2.2.2]oct-3-yl)(5-(3-chlorophenyl)furan-2-carboxamide)

Prepared by a method analogous to that described in Example 1 from (R)-N-(1-azabicyclo[2.2.2]oct-3-yl)(5-bromofuran-2-carboxamide) and 3-chlorophenylboronic acid, using tetrakis(triphenylphosphine)palladium(0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. After drying under vacuum, the hydrochloride salt of the title compound was obtained as a colourless solid; MS (ES$^+$) 331 (MH$^+$).

Example 39

(R)-N-(1-Azabicyclo[2.2.2]oct-3-yl)(5-(3-(N-acetylamino)phenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-(N-acetylamino)phenylboronic acid, using tetrakis(triphenylphosphine)palladium (0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 370 (MH$^+$).

Example 40

(R)-N-(1-Azabicyclo[2.2.2]oct-3-yl)(5-(3-fluorophenyl)thiophene-2-carboxamide)

Prepared by a method analogous to that described in Example 1 from (R)-N-(1-Azabicyclo[2.2.2]oct-3-yl)(5-bromothiophene-2-carboxamide) and 3-fluorophenylboronic acid, using tetrakis(triphenylphosphine)palladium (0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 331 (MH$^+$).

Example 41

(R)-N-(1-Azabicyclo[2.2.2]oct-3-yl)(5-(3-methoxyphenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-methoxyphenylboronic acid, using tetrakis(triphenylphosphine)palladium(0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 343 (MH$^+$).

Example 42

(R)-N-(1-Azabicyclo[2.2.2]oct-3-yl)(5-(3-ethoxyphenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-ethoxyphenylboronic acid, using tetrakis(triphenylphosphine)palladium (0) and sodium carbonate in a mixture of tetrahydrofuran, ethanol, and water. The compound was purified by reverse phase HPLC on a Waters Bondapak® $C_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 357 (MH$^+$).

Example 43

(R)-N-(1-Azabicyclo[2.2.2]oct-3-yl)(5-(3,5-dimethylisoxazol-4-yl)furan-2-carboxamide)

Prepared by a method analogous to that described in Example 1 from (R)-N-(1-azabicyclo[2.2.2]oct-3-yl)(5-bromofuran-2-carboxamide) and 3,5 dimethylisoxazolyl-4-boronic acid, using tetrakis(triphenylphosphine)palladium(0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the hydrochloride salt of the title compound as a colourless solid; MS (ES$^+$) 316 (MH$^+$).

Example 44

(R)-N-(1-Azabicyclo[2.2.2]oct-3-yl)(5-(3,5-dimethylisoxazol-4-yl)thiophene-2-carboxamide)

Prepared by a method analogous to that described in Example 1 from (R)-N-(1-azabicyclo[2.2.2]oct-3-yl)(5-bromothiophene-2-carboxamide) and 3,5-dimethylisoxazolyl-4-boronic acid, using tetrakis(triphenylphosphine)palladium (0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the hydrochloride salt of the title compound as a colourless solid; MS (ES$^+$) 332 (MH$^+$).

Example 45

(R)-N-(1-Azabicyclo[2.2.2]oct-3-yl)(5-(3-aminophenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-aminophenylboronic acid hydrochloride, using tetrakis(triphenylphosphine)palladium (0) and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a colourless solid; MS (ES$^+$) 328 (MH$^+$).

Example 46

(R)-N-(1-Azabicyclo[2.2.2]oct-3-yl)(5-(3-pyridyl)thiophene-3-carboxamide)

Prepared by a method analogous to that described in Example 1 from (R)-N-(1-azabicyclo[2.2.2]oct-3-yl)(5-bromothiophene-3-carboxamide) and pyridine-3-boronic acid, using tetrakis(triphenylphosphine)palladium (0), and sodium carbonate in a mixture of 1,2-dimethoxyethane and water. The compound was purified by reverse phase HPLC on a Waters Bondapak® $C_{18}$ column using a gradient of acetonitrile and 0.1% aqueous trifluoroacetic acid as the eluent. The product-containing fractions were then evaporated and the residue dissolved in methanol. Excess hydrogen chloride solution (1M in diethyl ether) was added and the solution was evaporated. Recrystallisation from methanol/diethyl ether gave the dihydrochloride salt of the title compound as a colourless solid; MS (ES$^+$) 314 (MH$^+$).

Example 47

(R)-N-(1-Azabicyclo[2.2.2]oct-3-yl)(5-(4-chlorophenyl)furan-2-carboxamide)

Prepared by a method analogous to that described in Example 1 from (R)-1-azabicyclo[2.2.2]oct-3-ylamine dihydrochloride and 5-(4-chlorophenyl)furoic acid; the compound was purified by chromatography on silica gel using ammoniated methanol/chloroform mixtures as the eluent; MS (ES$^+$) 331, 333 (MH$^+$).

Example 48

(R)-N-(1-Azabicyclo[2.2.2]oct-3-yl)(2-(3-pyridyl)thiazole-4-carboxamide)

A mixture of (R)-N-1-azabicyclo[2.2.2]oct-3-ylamine dihydrochloride (294 mg), 2-(3-pyridyl)thiazole-4-carboxylic acid (304 mg), 1-hydroxybenzotriazole hydrate (199 mg), O-benzotriazol-1-yl-N,N,N',N'-tetramethyluronium tetrafluoroborate (473 g), and N,N-diisopropylethylamine (1.0 mL) in N,N-dimethylformamide (10 mL) was stirred at room temperature overnight. The solution was evaporated, and the residue was partitioned between aqueous sodium hydroxide and chloroform. The solution was evaporated and the residue was purified by reverse phase HPLC on a Waters Bondapak® $C_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid (428 mg); MS (ES$^+$) 315 (MH$^+$).

Example 49

(R)-N-(1-Azabicyclo[2.2.2]oct-3-yl)(2-(4-pyridyl)thiazole-4-carboxamide)

A mixture of (R)-N-1-azabicyclo[2.2.2]oct-3-ylamine dihydrochloride (236 mg), 2-(4-pyridyl)thiazole-4-carboxylic acid (243 mg), 1-hydroxybenzotriazole hydrate (159 mg), O-benzotriazol-1-yl-N,N,N',N'-tetramethyluronium tetrafluoroborate (379 mg), and N,N-diisopropylethylamine (0.82 mL) in N,N-dimethylformamide (10 mL) was stirred at room temperature overnight. The solution was evaporated, and the residue was partitioned between aqueous sodium hydroxide and chloroform. The solution was evaporated and the residue was purified by reverse phase HPLC on a Waters Bondapak® $C_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid (428 mg); MS (ES$^+$) 315 (MH$^+$).

Example 50

(R)-N-(1-Azabicyclo[2.2.2]oct-3-yl)(5-(3-(N,N-dimethylamino)phenyl)thiophene-2-carboxamide)

Formaldehyde (37% solution in water, 0.18 mL) was added to a solution of (R)-N-(1-azabicyclo[2.2.2]oct-3-yl) (5-(3-aminophenyl)-thiophene-2-carboxamide) (92 mg) in 1% acetic acid in methanol (5 mL). After 30 minutes at room temperature, sodium cyanoborohydride (35 mg) was added, and the reaction mixture was stirred at room temperature for 1 h. The solution was evaporated and the residue was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid (54 mg); MS (ES$^+$) 356 (MH$^+$).

Example 51

(R)-N-(1-Azabicyclo[2.2.2]oct-3-yl)(5-(8-quinolinyl) thiophene-2-carboxamide)

Prepared by a method analogous to that described in Example 1 from (R)-N-(1-aza-bicyclo[2.2.2]oct-3-yl)(5-bromothiophene-2-carboxamide) and 8-quinolineboronic acid, tetrakis(triphenylphosphine)palladium (0), sodium carbonate in a mixture of DME, and water.

The compound was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid; MS (ES$^+$) 364 (MH$^+$).

Example 52

(S)-N-(1-Azabicyclo[2.2.2]oct-3-yl)(5-(3-pyridyl) thiophene-2-carboxamide)

Prepared by a method analogous to that described in Example 1 from (S)-N-(1-aza-bicyclo[2.2.2]oct-3-yl)(5-bromothiophene-2-carboxamide) and pyridine-3-boronic acid, using tetrakis(triphenylphosphine)palladium (0) and sodium carbonate in a mixture of tetrahydrofuran, ethanol and water. The compound was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid; MS (ES$^+$) 314 (MH$^+$).

Example 53

(S)-N-(1-Azabicyclo[2.2.2]oct-3-yl)(5-(4-pyridyl) thiophene-2-carboxamide)

Prepared by a method analogous to that described in Example 1 from (S)-N-(1-azabicyclo[2.2.2]oct-3-yl)(5-bromothiophene-2-carboxamide) and pyridine-4-boronic acid, using tetrakis(triphenylphosphine)palladium (0) and sodium carbonate in a mixture of 1,2-dimethoxyethane and water. The compound was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid; MS (ES$^+$) 314 (MH$^+$).

Example 54

(S)-N-(1-Azabicyclo[2.2.2]oct-3-yl)(5-(2-pyridyl) thiophene-2-carboxamide)

Prepared by a method analogous to that described in Example 27 from (S)-N-(1-azabicyclo[2.2.2]oct-3-yl)(5-bromothiophene-2-carboxamide) and 2-(tri-n-butylstannyl) pyridine. The compound was purified by flash chromatography 5%–20% 3.5N ammoniated methanol/chloroform mixture as eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid; MS (ES$^+$) 314 (MH$^+$)

Example 55

(S)-N-(1-Azabicyclo[2.2.2]oct-3-yl)(5-phenylthiophene-2-carboxamide)

Prepared by a method analogous to that described in Example 1 from (S)-N-(1-azabicyclo[2.2.2]oct-3-yl)(5-bromothiophene-2-carboxamide) and phenylboronic acid, tetrakis(triphenylphosphine)palladium (0) and sodium carbonate in a mixture of tetrahydrofuran, ethanol and water. The compound was purified by reverse phase HPLC on a Waters Bondapak® C$_{18}$ column using a gradient of acetonitrile and 0.1% aqueous trifluoroacetic acid as the eluent. Evaporation of the product-containing fractions gave the trifluoroacetate salt of the title compound as a colourless solid; MS (ES$^+$) 313 (MH$^+$).

Example 56

(R)-N-(1-Azabicyclo[2.2.2]oct-3-yl)(5-phenylthiophene-3-carboxamide)

Prepared by a method analogous to that described in Example 1 from (R)-N-(1-Aza-bicyclo[2.2.2]oct-3-yl)(5-bromothiophene-3-carboxamide) and phenylboronic acid, using tetrakis(triphenylphosphine)palladium(0), and sodium carbonate in a mixture of tetrahydrofuran, ethanol and water. The compound was purified by reverse phase HPLC on a Waters Bondapak® C$_{18}$ column using a gradient of acetonitrile and 0.1% aqueous trifluoroacetic acid as the eluent.

Evaporation of the product-containing fractions gave the trifluoroacetate salt of the title compound as a colourless solid; MS (ES$^+$) 313 (MH$^+$).

Example 57

(R)-N-(1-Azabicyclo[2.2.2]oct-3-yl)(4-phenylthiophene-2-carboxamide)

Prepared by a method analogous to that described in Example 1 from (R)-N-(1-Aza-bicyclo[2.2.2]oct-3-yl)(4-bromothiophene-2-carboxamide) and phenylboronic acid, using tetrakis(triphenylphosphine)palladium (0) and sodium carbonate in a mixture of tetrahydrofuran, ethanol, and water. The compound was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from ethyl acetate gave the hydrochloride salt of the title compound as a colourless solid; MS (ES$^+$) 313 (MH$^+$).

Example 58

(R)-N-(1-Azabicyclo[2.2.2]oct-3-yl)(5-(3-cyanophenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-cyanophenylboronic acid, using tetrakis(triphenylphosphine)palladium(0), and sodium carbonate in a mixture of tetrahydrofuran, ethanol and water. The compound was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the hydrochloride salt of the title compound as a colourless solid; MS (ES$^+$) 338 (MH$^+$).

Example 59

(R)-N-(1-Azabicyclo[2.2.2]oct-3-yl)(5-(3-(N-methylamino)phenyl)thiophene-2-carboxamide)

Sodium methoxide (14 mL, 0.5M solution in methanol) was added to the solution of (R)-N-(1-azabicyclo[2.2.2]oct-3-yl)(5-(3-aminophenyl)thiophene-2-carboxamide) (550 mg) in methanol (5 mL), then paraformaldehyde (117 mg) was added. The mixture was heated under reflux for 1 h. After cooling the reaction mixture to room temperature, sodium borohydride (175 mg) was added, and the solution was then heated under reflux for 2 h. Aqueous potassium hydroxide (1M, 1.4 mL) was added. Heating under reflux was resumed for 2 h and the reaction mixture was then left at room temperature for 16 h. The solvent was evaporated and the residue was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a colourless solid (120 mg); MS (ES$^+$) 342 (MH$^+$).

Example 60

(R)-N-(1-Azabicyclo[2.2.2]oct-3-yl)(5-(3-hydroxyphenyl)thiophene-2-carboxamide)

To the (R)-N-(1-azabicyclo[2.2.2]oct-3-yl)(5-(3-methoxyphenyl)thiophene-2-carboxamide) (900 mg), 48% aqueous hydrobromic acid (10 mL) and glacial acetic acid (10 mL) were added. After heating under reflux for 4 h, saturated aqueous sodium carbonate and solid sodium carbonate were added to adjust to pH 10. The aqueous layer was extracted with chloroform and the combined extracts were dried over magnesium sulfate. After filtration and evaporation, residue was purified by flash chromatography using 5%–20% 3.5M methanolic ammonia/chloroform mixtures as the eluent. The product obtained was purified by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the hydrochloride salt of the title compound as a colourless solid (32 mg); MS (ES$^+$) 329 (MH$^+$).

Example 61

(R)-N-(1-Azabicyclo[2.2.2]oct-3-yl)(5-(3-pyridylamino)thiophene-2-carboxamide)

The mixture of (R)-N-(1-azabicyclo[2.2.2]oct-3-yl)(5-bromothiophene-2-carboxamide) (315 mg), 3-aminopyridine (188 mg), tris(dibenzylideneacetone)dipalladium (0) (46 mg), racemic-2,2'-bis(diphenylphosphino)-1,1'-binaphthyl (62 mg), and sodium t-butoxide (192 mg) in tetrahydrofuran (10 mL) was heated under reflux for 20 h. The mixture was filtered and the residue was purified by flash chromatography using 5%–20% 3.5M methanolic ammonia/chloroform mixtures as the eluent. The compound was purified further by reverse phase HPLC on a Waters Bondapak® C$_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as a yellow solid (77 mg); MS (ES$^+$) 329 (MH$^+$).

Example 62

(R)-N-(1-Azabicyclo[2.2.2]oct-3-yl)(5-(3-chlorophenyl)thiophene-2-carboxamide)

Prepared by a method analogous to that described in Example 1 from (R)-N-(1-azabicyclo[2.2.2]oct-3-yl)(5-bromothiophene-2-carboxamide) and 3-chlorophenylboronic acid, using tetrakis(triphenylphosphine)palladium (0) and sodium carbonate in a mixture of tetrahydrofuran, ethanol and water. The compound was purified by flash chromatography using a gradient of 5%–20% 3.5M methanolic ammonia/chloroform mixtures as the eluent to give the title compound as a colourless solid; MS (ES$^+$) 347 (MH$^+$).

Example 63

(R)-N-(1-Azabicyclo[2.2.2]oct-3-yl)(5-(3-(4-morpholinyl)phenyl)thiophene-2-carboxamide)

A mixture of (R)-N-(1-azabicyclo[2.2.2]oct-3-yl)(5-(3-chlorophenyl)thiophene-2-carboxamide) (0.98 g), morpholine (0.5 mL), tris(dibenzylideneacetone)dipalladium(0) (132 mg), racemic-2,2'-bis(diphenylphosphino)-1,1'-binaphthyl (180 mg), and sodium t-butoxide (554 mg) in tetrahydrofuran (25 mL) was heated under reflux for 20 hr under nitrogen. The mixture was filtered and the residue was purified by flash chromatography using a gradient of 5%–20% 3.5M methanolic ammonia/chloroform mixtures as the eluent. The mixture was then subjected to reverse phase HPLC on a Waters Bondapak® $C_{18}$ column using a gradient of acetonitrile and 0.1% aqueous trifluoroacetic acid as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as solid (400 mg); MS (ES$^+$) 398(MH$^+$).

Example 64

(R)-N-(1-Azabicyclo[2.2.2]oct-3-yl)(5-(3-(aminomethyl)phenyl)thiophene-2-carboxamide)

To the solution of (R)-N-(1-azabicyclo[2.2.2]oct-3-yl)(5-(3-cyanophenyl)thiophene-2-carboxamide) (311 mg) in methanol and acetic acid (1: 1,10 mL) a catalytic amount of 10% Pd-C was added and the mixture was hydrogenated at 50 p.s.i. for 36 hr. The mixture was filtered through a pad of celite. The residue was purified first by flash chromatography using 5–20% 3.5M methanolic ammonia/chloroform mixtures as the eluent and then by reverse phase IHPLC on a Waters Bondapak® $C_{18}$ column using a gradient of acetonitrile and 0.1% aqueous trifluoroacetic acid as the eluent. The free base was prepared by basification of the product-containing fractions and extraction into chloroform followed by evaporation to gave the title compound (23 mg); MS (ES$^+$) 342 (MH$^+$).

Example 65

(R)-N-(1-Azabicyclo[2.2.2]oct-3-yl)(5-phenoxythiophene-2-carboxamide)

To a solution of (R)-N-(1-azabicyclo[2.2.2]oct-3-yl)(5-bromothiophene-2-carboxamide) (463 mg) in pyridine (10 mL) phenol (158 mg), copper iodide (32 mg) and potassium carbonate (97 mg) were added. The mixture was stirred at 125° C. for 65 h under nitrogen. Water was added and the aqueous layer was extracted with chloroform. Following evaporation, the residue was purified by flash chromatography using 5–20% 3.5M methanolic ammonia/chloroform mixtures as the eluent and then by reverse phase HPLC on a Waters Bondapak® $C_{18}$ column using a gradient of acetonitrile and 0.1% aqueous trifluoroacetic acid as the eluent. The free base was prepared by basification of the product-containing fractions and extraction into chloroform followed by evaporation to gave the title compound (80 mg); MS (ES$^+$) 329 (MH$^+$).

Example 66

(R)-N-(1-Azabicyclo[2.2.2]oct-3-yl)(5-(3-aminophenyl)furan-2-carboxamide)

Prepared by a method analogous to that described in Example 1 from (R)-N-(1-azabicyclo[2.2.2]oct-3-yl)(5-bromofuran-2-carboxamide) and 3-aminophenylboronic acid, using tetrakis(triphenylphosphine)palladium (0) and sodium carbonate in a mixture of tetrahydrofuran, ethanol and water. The compound was purified by flash chromatography using 5–20% 3.5M methanolic ammonia/chloroform mixtures as the eluent and then by reverse phase HPLC on a Waters Bondapak® $C_{18}$ column using a gradient of acetonitrile and 0.1% aqueous trifluoroacetic acid as the eluent. The free base was prepared by basification of the product-containing fractions and extraction into chloroform followed by evaporation to gave the title compound; MS (ES$^+$) 312 (MH$^+$).

Example 67

(R)-N-(1-Azabicyclo[2.2.2]oct-3-yl)(5-(3-(N,N-dimethylamino)phenyl)furan-2-carboxamide)

To the solution of (R)-N-(1-azabicyclo[2.2.2]oct-3-yl)(5-(3-aminophenyl)furan-2-carboxamide) (220 mg) in 1% acetic acid in ethanol (10 mL) formaldehyde (0.26 mL) was added. After 45 min, sodium cyanoborohydride (89 mg) was added. The mixture was stirred for 4 h. Water was added and the solution was basified to pH>10 by adding solid sodium carbonate. The aqueous layer was extracted chloroform and the extracts were dried over magnesium sulfate, filtered and evaporated. The compound was purified by flash chromatography using 5–20% 3.5M methanolic ammonia/chloroform mixtures as the eluent. The hydrochloride salt was prepared by evaporation of the product-containing fractions, dissolution of the residue in methanol, addition of excess hydrogen chloride solution (1M in diethyl ether) and evaporation. Recrystallisation from methanol/diethyl ether gave the dihydrochloride salt of the title compound as solid (141 mg); MS (ES$^+$) 340 (MH$^+$).

Example 68

(R)-N-(1-Azabicyclo[2.2.2]oct-3-yl)(5-(3-formylphenyl)thiophene-2-carboxamide)

Prepared by a method analogous to that described in example 1 from (R)-N-(1-aza-bicyclo[2.2.2]oct-3-yl)(5-bromothiophene-2-carboxamide) and 3-formylphenyl boronic acid, tetrakis(triphenylphosphine)palladium (0), sodium carbonate in a mixture of tetrahydrofuran, ethanol and water. The compound was purified by reverse phase HPLC on a Waters Bondapak® $C_{18}$ column using a gradient of acetonitrile and 0.1% aqueous trifluoroacetic acid as the eluent. The free base was prepared by basification of the product-containing fractions. The aqueous layer was extracted by chloroform and evaporated to gave the title compound; MS (ES$^+$) 341 (MH$^+$)

Example 69

(R)-N-(1-Azabicyclo[2.2.2]oct-3-yl)(5-(3-(hydroxymethyl)phenyl)thiophene-2-carboxamide)

To the solution of (R)-N-(1-azabicyclo[2.2.2]oct-3-yl)(5-(3-formylphenyl)thiophene-2-carboxamide) (875 mg) in methanol (15 mL), sodium borohydride (97.2 mg) was added. The mixture was then stirred at room temperature for 4 h. The residue was partitioned between water and chloroform. The extracts were dried over magnesium sulfate, filtered, and evaporated, and the residue was then purified by flash chromatography using 5–20% 3.5M methanolic ammonia/chloroform mixtures as the eluent to give the title compound (547 mg); MS (ES$^+$) 343 (MH$^+$).

What is claimed is:

1. A compound of formula I:

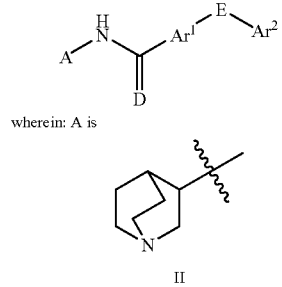

wherein: A is

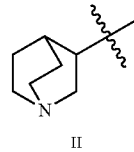

D is oxygen or sulfur;
E is a single bond, oxygen, sulfur, or NR$^{10}$;
Ar$^1$ is a 5-membered heteroaromatic ring containing one sulfur atom;
Ar$^2$ is a phenyl or a 5- or 6-membered aromatic or heteroaromatic ring containing 1, 2 or 3 atoms selected from nitrogen, oxygen or sulfur atoms, wherein there is no more than 2 oxygen or sulfur atom; or naphthyl or an 8-, 9- or 10-membered fused aromatic or heteroaromatic ring system containing 1, 2 or 3 nitrogen, oxygen or sulfur atoms, wherein there is no more than 2 oxygen or sulfur atoms;
wherein the aromatic rings Ar$^1$ and Ar$^2$ are substituted with 0, 1, 2 or 3 substituents selected from halogen, C$_{1-4}$alkyl, C$_{2-4}$alkenyl, C$_{2-4}$alkynyl, CN, NO$_2$, NR$^1$R$^2$, CH$_2$NR$^1$R$^2$, OR$^3$, CH$_2$OR$^3$, CO$_2$R$^4$ and CF$_3$;
R$^1$, R$^2$, and R$^3$ are independently C$_{1-4}$alkyl, aryl, heteroaryl, C(O)R$^5$, C(O)NHR$^6$, C(O)R$^7$, SO$_2$R$^8$; or R$^1$ and R$^2$ may together be (CH$_2$)$_j$G(CH$_2$)$_k$ where G is oxygen, sulfur, NR$^9$, or a single bond;
j is 2, 3 or 4;
k is 0, 1 or 2;
R$^4$, R$^5$, R$^6$, R$^7$, R$^8$, R$^9$, and R$^{10}$ are independently C$_{1-4}$alkyl, aryl, or heteroaryl;
or an enantiomer thereof or pharmaceutically-acceptable salts thereof.

2. A compound according to claim 1, wherein D represents oxygen.

3. A compound according to claim 2, wherein E represents a single bond.

4. A compound according to claim 2, wherein E represents oxygen or NR$^{10}$.

5. A compound according claim 1, wherein Ar$^2$ represents phenyl or a 5- or 6-membered heteroaromatic ring containing 1, 2 or 3 atoms selected from nitrogen, oxygen or sulfur atoms, wherein there is no more that 2 oxygen or sulfur atoms; or pharmaceutically-acceptable salts thereof.

6. A compound according to claim 5, wherein Ar$^2$ represents a phenyl, furyl, thiophenyl, or pyridinyl.

7. A compound according to claim 6, wherein Ar$^1$ is substituted with the carboxamide or thiocarboxamide group C(=D)NHA, but no further substituents.

8. A compound according to claim 7, in which the -EAr$^2$ and the carboxamide or thiocarboxamide group C(=D)NHA substituents on Ar$^1$ are positioned in a 1,3-relationship relative to each other.

9. A compound according to claim 6, wherein Ar$^1$ or Ar$^2$ is substituted with zero or one substituents selected from: halogen, C$_{1-4}$alkyl, C$_{2-4}$alkenyl, C$_{2-4}$alkynyl, CN, NO$_2$, NR$^1$R$^2$, CH$_2$NR$^1$R$^2$, OR$^3$, CH$_2$OR$^3$, CO$_2$R$^4$, and CF$_3$.

10. A compound according claim 1, wherein Ar$^1$ is substituted with the carboxamide or thiocarboxamide group C(=D)NHA, but no further substituents.

11. A compound according to claim 10, in which the -EAr$^2$ and the carboxamide or thiocarboxamide group C(=D)NHA substituents on Ar$^1$ are positioned in a 1,3-relationship relative to each other.

12. A compound according to claim 1, wherein Ar$^1$ or Ar$^2$ is substituted with zero or one substituents selected from: halogen, C$_{1-4}$alkyl, C$_{2-4}$alkenyl, C$_{2-4}$alkynyl, CN, NO$_2$, NR$^1$R$^2$, CH$_2$NR$^1$R$^2$, OR$^3$, CH$_2$OR$^3$, CO$_2$R$^3$, and CF$_3$.

13. A compound according to claim 1 wherein:
A represents:

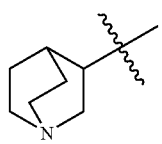

D represents oxygen;
E represents a single bond;
Ar$^1$ is a 5-membered heteroaromatic ring containing one sulfur atom;
Ar$^2$ is phenyl or a 5- or 6-membered heteroaromatic ring containing 1, 2 or 3 atoms selected from nitrogen, oxygen or sulfur atoms, wherein there is no more than 2 oxygen or sulfur atoms;
Ar$^1$ is substituted with Ar$^2$ and the carboxamide group C(=O)NHA, but no further substituents; and
Ar$^2$ is substituted with zero or one substituents selected from: halogen, C$_{1-4}$alkyl, C$_{2-4}$alkenyl, C$_{2-4}$alkynyl, CN, NO$_2$, NR$^1$R$^2$, CH$_2$NR$^1$R$^2$, OR$^3$, CH$_2$OR$^3$, CO$_2$OR$^3$, and CF$_3$.

14. A compound according to claim 13, wherein Ar$^1$ represents a thiophene ring; or an enantiomer thereof, or a pharmaceutically-acceptable salt thereof.

15. A compound according to claim 1, wherein:
A represents:

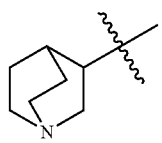

D represents oxygen;
E represents an oxygen or NH;
Ar$^1$ is a 5-membered heteroaromatic ring containing one sulfur atom;
Ar$^2$ is phenyl or a 5- or 6-membered heteroaromatic ring containing 1, 2 or 3 atoms selected from nitrogen, oxygen or sulfur atoms, wherein there is no more than 2 oxygen or sulfur atoms;

Ar¹ is substituted with EAr² and the C(=O)NHA group, but no further substituents;

Ar² is substituted with zero or one substituents selected from halogen, $C_{1-4}$alkyl, $C_{2-4}$alkenyl, $C_{2-4}$alkynyl, CN, $NO_2$, $NR^1R^2$, $CH_2NR^1R^2$, $OR^3$, $CH_2OR^3$, $CO_{2R}^4$, and $CF_3$.

16. A compound according to claim 15, wherein Ar¹ represents a thiophene ring; or an enantiomer thereof, or pharmaceutically-acceptable salts thereof.

17. A compound according to claim 16, in which the EAr² and the carboxamide group, C(=O)NHA on Ar¹, are positioned in a 1,3-relationship relative to each other; or an enantiomer thereof, or pharmaceutically-acceptable salts thereof.

18. A compound according to claim 1, said compound being selected from the group of:
N-(1-Azabicyclo[2.2.2]oct-3-yl)(5-phenylthiophene-2-carboxamide);
N-(1-Azabicyclo[2.2.2]oct-3-yl)(5-(4-pyridyl)thiophene-2-carboxamide);
N-(1-Azabicyclo[2.2.2]oct-3-yl)(5-(3-pyridyl)thiophene-2-carboxamide);
N-(1-Azabicyclo[2.2.2]oct-3-yl)(5-(2-pyridyl)thiophene-2-carboxamide);
N-(1-Azabicyclo[2.2.2]oct-3-yl)(5-(3-(N-acetylamino)phenyl)thiophene-2-carboxamide);
N-(1-Azabicyclo[2.2.2]oct-3-yl)(5-(3-fluorophenyl)thiophene-2-carboxamide);
N-(1-Azabicyclo[2.2.2]oct-3-yl)(5-(3-methoxyphenyl)thiophene-2-carboxamide);
N-(1-Azabicyclo[2.2.2]oct-3-yl)(5-(3-ethoxyphenyl)thiophene-2-carboxamide);
N-(1-Azabicyclo[2.2.2]oct-3-yl)(5-(3,5-dimethylisoxazol-4-yl)thiophene-2-carboxamide);
N-(1-Azabicyclo[2.2.2]oct-3-yl)(5-(3-aminophenyl)thiophene-2-carboxamide);
N-(1-Azabicyclo[2.2.2]oct-3-yl)(5-(3-(N,N-dimethylamino)phenyl)thiophene-2-carboxamide);
N-(1-Azabicyclo[2.2.2]oct-3-yl)(5-(8-quinolinyl)thiophene-2-carboxamide);
N-(1-Azabicyclo[2.2.2]oct-3-yl)(5-(3-pyridyl)thiophene-2-carboxamide);
N-(1-Azabicyclo[2.2.2]oct-3-yl)(5-(4-pyridyl)thiophene-2-carboxamide);
N-(1-Azabicyclo[2.2.2]oct-3-yl)(5-(2-pyridyl)thiophene-2-carboxamide);
N-(1-Azabicyclo[2.2.2]oct-3-yl)(5-phenylthiophene-2-carboxamide);
N-(1-Azabicyclo[2.2.2]oct-3-yl)(5-(3-cyanophenyl)thiophene-2-carboxamide);
N-(1-Azabicyclo[2.2.2]oct-3-yl)(5-(3-hydroxyphenyl)thiophene-2-carboxamide);
N-(1-Azabicyclo[2.2.2]oct-3-yl)(5-(3-pyridylamino)thiophene-2-carboxamide);
N-(1-Azabicyclo[2.2.2]oct-3-yl)(5-(3-chlorophenyl)thiophene-2-carboxamide);
N-(1-Azabicyclo[2.2.2]oct-3-yl)(5-(3-(4-morpholinyl)phenyl)thiophene-2-carboxamide);
N-(1-Azabicyclo[2.2.2]oct-3-yl)(5-(3-(aminomethyl)phenyl)thiophene-2-carboxamide);
N-(1-Azabicyclo[2.2.2]oct-3-yl)(5-(3-formylphenyl)thiophene-2-carboxamide);
N-(1-Azabicyclo[2.2.2]oct-3-yl)(5-(3-(hydroxymethyl)phenyl)thiophene-2-carboxamide);
N-(1-Azabicyclo[2.2.2]oct-3-yl)(4-(2-pyridyl)thiophene-2-carboxamide);
N-(1-Azabicyclo[2.2.2]oct-3-yl)(4-(4-pyridyl)thiophene-2-carboxamide);
N-(1-Azabicyclo[2.2.2]oct-3-yl)(4-(3-pyridyl)thiophene-2-carboxamide);
N-(1-Azabicyclo[2.2.2]oct-3-yl)(4-phenylthiophene-2-carboxamide);
N-(1-Azabicyclo[2.2.2]oct-3-yl)(5-phenylthiophene-3-carboxamide), and
N-(1-Azabicyclo[2.2.2]oct-3-yl)(5-(3-pyridyl)thiophene-3-carboxamide),
or a pharmaceutically-acceptable salt thereof.

19. A compound according to claim 1, said compound being selected from the group of:
(R)-N-(1-Azabicyclo[2.2.2]oct-3-yl)(5-phenylthiophene-2-carboxamide);
(R)-N-(1-Azabicyclo[2.2.2]oct-3-yl)(5-(4-pyridyl)thiophene-2-carboxamide);
(R)-N-(1-Azabicyclo[2.2.2]oct-3-yl)(5-(3-pyridyl)thiophene-2-carboxamide);
(R)-N-(1-Azabicyclo[2.2.2]oct-3-yl)(5-(2-pyridyl)thiophene-2-carboxamide);
(R)-N-(1-Azabicyclo[2.2.2]oct-3-yl)(5-(3-(N-acetylamino)phenyl)thiophene-2-carboxamide);
(R)-N-(1-Azabicyclo[2.2.2]oct-3-yl)(5-(3-fluorophenyl)thiophene-2-carboxamide);
(R)-N-(1-Azabicyclo[2.2.2]oct-3-yl)(5-(3-methoxyphenyl)thiophene-2-carboxamide);
(R)-N-(1-Azabicyclo[2.2.2]oct-3-yl)(5-(3-ethoxyphenyl)thiophene-2-carboxamide);
(R)-N-(1-Azabicyclo[2.2.2]oct-3-yl)(5-(3,5-dimethyl-isoxazol-4-yl)thiophene-2-carboxamide);
(R)-N-(1-Azabicyclo[2.2.2]oct-3-yl)(5-(3-aminophenyl)thiophene-2-carboxamide);
(R)-N-(1-Azabicyclo[2.2.2]oct-3-yl)(5-(3-(N,N-dimethylamino)phenyl)thiophene-2-carboxamide);
(R)-N-(1-Azabicyclo[2.2.2]oct-3-yl)(5-(8-quinolinyl)thiophene-2-carboxamide);
(S)-N-(1-Azabicyclo[2.2.2]oct-3-yl)(5-(3-pyridyl)thiophene-2-carboxamide);
(S)-N-(1-Azabicyclo[2.2.2]oct-3-yl)(5-(4-pyridyl)thiophene-2-carboxamide);
(S)-N-(1-Azabicyclo[2.2.2]oct-3-yl)(5-(2-pyridyl)thiophene-2-carboxamide);
(S)-N-(1-Azabicyclo[2.2.2]oct-3-yl)(5-phenylthiophene-2-carboxamide);
(R)-N-(1-Azabicyclo[2.2.2]oct-3-yl)(5-(3-cyanophenyl)thiophene-2-carboxamide);
(R)-N-(1-Azabicyclo[2.2.2]oct-3-yl)(5-(3-hydroxyphenyl)thiophene-2-carboxamide);
(R)-N-(1-Azabicyclo[2.2.2]oct-3-yl)(5-(3-pyridylamino)thiophene-2-carboxamide);
(R)-N-(1-Azabicyclo[2.2.2]oct-3-yl)(5-(3-chlorophenyl)thiophene-2-carboxamide);
(R)-N-(1-Azabicyclo[2.2.2]oct-3-yl)(5-(3-(4-morpholinyl)phenyl)thiophene-2-carboxamide);
(R)-N-(1-Azabicyclo[2.2.2]oct-3-yl)(5-(3-(aminomethyl)phenyl)thiophene-2-carboxamide);
(R)-N-(1-Azabicyclo[2.2.2]oct-3-yl)(5-(3-formylphenyl)thiophene-2-carboxamide);
(R)-N-(1-Azabicyclo[2.2.2]oct-3-yl)(5-(3-(hydroxymethyl)phenyl)thiophene-2-carboxamide);
(R)-N-(1-Azabicyclo[2.2.2]oct-3-yl)(4-(2-pyridyl)thiophene-2-carboxamide);
(R)-N-(1-Azabicyclo[2.2.2]oct-3-yl)(4-(4-pyridyl)thiophene-2-carboxamide);
(R)-N-(1-Azabicyclo[2.2.2]oct-3-yl)(4-(3-pyridyl)thiophene-2-carboxamide);

(R)-N-(1-Azabicyclo[2.2.2]oct-3-yl)(4-phenylthiophene-2-carboxamide);

(R)-N-(1-Azabicyclo[2.2.2]oct-3-yl)(5-phenylthiophene-3-carboxamide), and (R)-N-(1-Azabicyclo[2.2.2]oct-3-yl)(5-(3-pyridyl)thiophene-3-carboxamide), or a pharmaceutically-acceptable salt thereof.

20. A method of treatment of human diseases or conditions in which activation of the α7 nicotinic receptor is beneficial wherein the diseases or condition is Alzheimer's disease, learning deficit, cognition deficit, attention deficit, memory loss, Lewy Body Dementia, Attention Deficit Hyperactivity Disorder, anxiety, schizophrenia, mania or manic depression, which comprises administering a therapeutically effective amount of a compound as defined in any one of claims 1 to 19.

21. A process for the preparation of a compound of formula I, as defined in any one of claims 1 to 19, which comprises:

reacting a compound of formula VI:

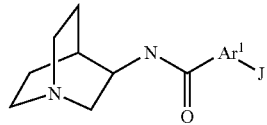

VI wherein J represents halogen, or $OSO_2CF_3$ substituent at the position of ring $Ar^1$ at which the bond to ring $Ar^2$ is formed with a organometallic compound of formula VII;

$Ar^2$-M                    VII wherein M represents $B(OH)_2$, trimethylstannyl or tri-n-butylstannyl;

in the presence of a organometallic catalyst and solvent.

* * * * *